(12) United States Patent
Bhaumik et al.

(10) Patent No.: US 9,778,263 B2
(45) Date of Patent: Oct. 3, 2017

(54) QUANTITATIVE IN SITU CHARACTERIZATION OF BIOLOGICAL SAMPLES

(71) Applicant: General Electric Company, Schenectady, NY (US)

(72) Inventors: Srabani Bhaumik, Schenectady, NY (US); Michael John Gerdes, Albany, NY (US); Zhengyu Pang, Clifton Park, NY (US); Fiona Ginty, Niskayuna, NY (US); Christopher James Sevinsky, Watervliet, NY (US); Qing Li, Niskayuna, NY (US); Alberto Santamaria-Pang, Schenectady, NY (US); Yunxia Sui, Clifton Park, NY (US); Keyur Hemantkumar Desai, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 304 days.

(21) Appl. No.: 14/079,347

(22) Filed: Nov. 13, 2013

(65) Prior Publication Data

US 2015/0133321 A1    May 14, 2015

(51) Int. Cl.
*G01N 33/574* (2006.01)
*G01N 33/569* (2006.01)
(Continued)

(52) U.S. Cl.
CPC . *G01N 33/57492* (2013.01); *G01N 33/54393* (2013.01); *G01N 33/56972* (2013.01);
(Continued)

(58) Field of Classification Search
CPC ....... G01N 33/57492; G01N 33/54393; G01N 33/56972; G01N 33/56977; G01N 1/30;
(Continued)

(56) References Cited

U.S. PATENT DOCUMENTS 7,629,125 B2 * 12/2009 Sood .................... G01N 33/542
                                                              435/6.16
7,741,045 B2    6/2010 Gerdes et al.
(Continued)

FOREIGN PATENT DOCUMENTS

WO    2008133729 A2    11/2008
WO    2010126452 A1    11/2010

OTHER PUBLICATIONS

Ovestad et al. Local immune response in the microenvironment of CIN2-3 with and without spontaneous regression. Modern Pathology 23: 1231-1240 (May 28, 2010).*
(Continued)

*Primary Examiner* — Gail R Gabel
(74) *Attorney, Agent, or Firm* — Pabitra K. Chakrabarti

(57) ABSTRACT

The present disclosure relates to characterization of biological samples. By way of example, a biological sample may be contacted with a plurality of probes specific for targets in the sample, such as probes for immune markers and segmenting probes. Acquired image data of the sample may be used to segment the images into epithelial and stromal regions to characterize individual cells in the sample based on the binding of the probes. Further, the biological sample may be characterized by a distribution, location, and type of a plurality of the characterized cells.

22 Claims, 15 Drawing Sheets

(51) Int. Cl.
G01N 33/543 (2006.01)
G06T 7/00 (2017.01)
G06K 9/00 (2006.01)
G01N 1/30 (2006.01)

(52) U.S. Cl.
CPC ... *G01N 33/56977* (2013.01); *G06K 9/00147* (2013.01); *G06T 7/0012* (2013.01); *G01N 1/30* (2013.01); *G06T 2207/10024* (2013.01); *G06T 2207/30024* (2013.01)

(58) Field of Classification Search
CPC .............. G06K 9/00147; G06T 7/0012; G06T 2207/10024; G06T 2207/30024
See application file for complete search history.

(56) References Cited

U.S. PATENT DOCUMENTS

| | | |
|---|---|---|
| 8,263,344 B2 | 9/2012 | Kroemer et al. |
| 8,300,938 B2 | 10/2012 | Can et al. |
| 8,440,798 B2 | 5/2013 | Clausen et al. |
| 8,455,686 B2 | 6/2013 | Koya et al. |
| 2008/0118518 A1 | 5/2008 | Cirrito et al. |
| 2009/0238457 A1* | 9/2009 | Rittscher .............. G06K 9/0014 382/171 |
| 2012/0100560 A1 | 4/2012 | Searson et al. |
| 2013/0061342 A1 | 3/2013 | Dylla et al. |
| 2013/0130226 A1 | 5/2013 | Lim et al. |
| 2014/0314299 A1 | 10/2014 | Santamaria-Pang et al. |

OTHER PUBLICATIONS

Can et al. Techniques for Cellular and Tissue-Based Image Quantitation of Protein Biomarkers. Microscopic Image Analysis for Lifescience Applications (Aug. 2008).*
Search Report and Written Opinion from corresponding PCT Application No. PCT/S2014/065185 dated Apr. 21, 2015, 12 pages.
Gerdes et al: "Highly multiplexed single-cell analysis of formalin-fixed, paraffin-emedded cancer tissue", Proceedings of the National Academy of Sciences, vol. 110, No. 29, Jul. 16, 2013, pp. 11982-11987.
Kruger et al: "Combat or surveillance? Evaluation of the heterogeneous inflammatory breast cancer microenvironment", The Journal of Pathology, vol. 229, No. 4, Feb. 15, 2013, pp. 569-578.
Ovestad et al: "Local immune response in the microenvironment of CIN2-3 with and without spontaneous regression", Modern Pathology, vol. 23, No. 9, May 28, 2010, pp. 1231-1240.
Gerdes et al: "Emerging Understand of Multiscale Tumor Heterogeneity", Frontiers in Oncology, vol. 4, Dec. 18, 2014.
Gerdes et al: "Highly multiplexed single-cell analysis of formalin-fixed, paraffin-embedded cancer tissue—supplementary information", Proceedings of the National Academy of Sciences, vol. 110, No. 29, Jul. 1, 2013, pp. 11982-11987.
Hanahan, D. et al., "Hallmarks of cancer: the next generation", Cell 2011, vol. 144 pp. 646-674.
Grivennikov, et al., "Immunity, inflammation, and cancer" Cell 2010, vol. 140 pp. 883-899.
Hanahan, D. et al., "Accessories to the crime: functions of cells recruited to the tumor microenvironment", Cancer cell 2012, vol. 21 pp. 309-322.
Reck, M., "What future opportunities may immuno-oncology provide for improving the treatment of patients with lung cancer?", Annals of Oncology:official journal of the European Society for Medical Oncology, ESMO Sep. 2012, vol. 23 Supplemental 8, pp. 28-34.
Fridman et al., "The immune contexture in human tumours: impact on clinical outcome", Nature Reviews Cancer Apr. 2012, vol. 12 pp. 298-306.

Fridman et al., "The Immune Microenvironment of Human Tumors: General Significance and Clinical Impact", Cancer Microenvironment 2013, vol. 6 pp. 117-122.
Mlecnik B., et al., "Tumor immunosurveillance in human cancers", Cancer Metastasis Reviews 2011, vol. 30 pp. 5-12.
Fridman, et al., "Immune infiltration in human cancer: prognostic significance and disease control", Current topics in microbiology and immunology 2011, vol. 344 pp. 1-24.
Denardo, et al., CD4(+) T cells regulate pulmonary metastasis of mammary carcinomas by enhancing protumor properties of macrophages, Cancer Cell 2009, vol. 16, pp. 91-102.
Galon, et al., "Type, density, and location of immune cells within human colorectal tumors predict clinical outcome", Science Sep. 2006, vol. 313, pp. 1960-1964.
Fridlender, et al., "Polarization of tumor-associated neutrophil phenotype by TGF-beta: "N1" versus "N2" TAN", Cancer Cell Sep. 2009, vol. 16, pp. 183-194.
Hoos, et al., "The immuno-oncology framework: Enabling a new era of cancer therapy", Oncoimmunology 2012, vol. 1 pp. 334-339.
El-Houseini, et al., "Isolation and Immuno-Phenotypic Characterization of Tumor Infiltrating Lymphocytes (TILs) Obtained from Breast Malignant Tumor Tissues of Egyptian Patients", Journal of the Egyptian National Cancer Institute Dec. 2008, vol. 20, No. 4, pp. 379-386.
Bendall, et al., "A deep profilers guide to cytometry", Trends in immunology, 2012, vol. 33, pp. 323-332.
Chow, et al., "Inflammation and immune surveillance in cancer", Seminars in Cancer Biology 2012, vol. 22, pp. 23-32.
Wolchok "How recent advances in immunotherapy are changing the standard of care for patients with metastatic melanoma", Annals of Oncology: official journal of the European Society for Medical Oncology, ESMO 2012, vol. 23, Supplement 8 pp. 15-21.
Gao, et al., "Advances in the development of cancer immunotherapies", Trends in immunology 2013, vol. 34, pp. 90-98.
McCoy, et al., "Peripheral CD8(+) T cell proliferation is prognostic for patients with advanced thoracic malignancies", Cancer Immunology Immunotherapy, CII 2013, vol. 62, pp. 529-539.
Wakabayashi, et al., "CD4+ T cells in cancer stroma, not CD8+ T cells in cancer cell nests, are associated with favorable prognosis in human non-small cell lung cancers", Cancer Science 2003, vol. 94, pp. 1003-1009.
Galon, et al., "Cancer classification using the Immunoscore: a worldwide task force", Journal of Translational Medicine 2012, vol. 10, No. 205, pp. 1-9.
Goding, et al., "Restoring Immune Function of Tumor-Specific CD4+ T Cells during Recurrence of Melanoma", Journal of Immunology 2013, vol. 190, pp. 4899-4909.
Myklebust, et al., "High PD-1 expression and suppressed cytokine signaling distinguish T cells infiltrating follicular lymphoma tumors from peripheral T cells", Blood 2013, vol. 121, pp. 1367-1376.
Butterfield, et al., "Recommendations from the iSBTc-SITC/FDA/NCI Workshop on Immunotherapy Biomarkers", Clinical cancer research:an official journal of the American Association for Cancer Research 2011, vol. 17, pp. 3064-3076.
Rosenberg, "Raising the bar: the curative potential of human", Cancer Immunotherapy, Science Translational Medicine Mar. 2012, vol. 4, Issue 127, pp. 1-5.
Iwai, et al., "Extended survival observed in adoptive activated T lymphocyte immunotherapy for advanced lung cancer: results of a multicenter historical cohort study", Cancer Immunology Immunotherapy, CII 2012, vol. 61, pp. 1781-1790.
Lee, et al., "Immune correlates of melanoma survival in adoptive cell therapy", OncoImmunology Feb. 2013, vol. 2:, Issue. 2, pp. e22889-1-9.
Pedrazzoli, et al., "Is adoptive T-cell therapy for solid tumors coming of age?", Bone Marrow Transplantation 2012, vol. 47, pp. 1013-1019.
Schneider, et al., "Foxp3(+) regulatory T cells and natural killer cells distinctly infiltrate primary tumors and draining lymph nodes in pulmonary adenocarcinoma", Journal of Thoracic Oncology:official publication of the International Association for the Study of Lung Cancer 2011, vol. 6, pp. 432-438.

(56) References Cited

OTHER PUBLICATIONS

Baumgarth, et al., "A practical approach to multicolor flow cytometry for immunophenotyping", Journal of Immunological Methods 2000, vol. 243, pp. 77-97.
Crotty, "Follicular helper CD4 T cells (TFH)", Annual review of immunology 2011, vol. 29, pp. 621-663.
Ame-Thomas, et al., "Characterization of intratumoral follicular helper T cells in follicular lymphoma: role in the survival of malignant B cells", Leukemia 2012, vol. 26, pp. 1053-1063.
Mahnke, et al., "Optimizing a multicolor immunophenotyping assay", Clinics in Laboratory Medicine 2007, vol. 27, pp. 469-485.
Klatka, et al., "Expression of selected regulatory molecules on the CD83+ monocyte-derived dendritic cells generated from patients with laryngeal cancer and their clinical significance", European Archives of Oto-Rhino-Laryngology 2013, vol. 270, 22 pages.
Chattopadhyay, et al., "Cytometry: today's technology and tomorrow's horizons", Methods 2012, vol. 57, pp. 251-258.
Leipold, et al., "Mass cytometry: protocol for daily tuning and running cell samples on a CyTOF mass cytometer", Journal of Visualized Experiments, JoVE 2012, vol. 69, e4398, 11 pages.
Takahashi, et al., "In situ quantitative immunoprofiling of regulatory T cells using laser scanning cytometry", Transplantation proceedings 2009, vol. 41, pp. 238-239.
Gerner, et al., "Histo-cytometry: a method for highly multiplex quantitative tissue imaging analysis applied to dendritic cell subset microanatomy in lymph nodes", Immunity 2012, vol. 37, pp. 364-376.
Fontenot, et al., "Foxp3 programs the development and function of CD4+CD25+ regulatory T cells", Nature Immunology, Apr. 2003; vol. 4, No. 4, pp. 330-336.
Pennock, et al., "Patient Responses to Ipilimumab, a Novel Immunopotentiator for Metastatic Melanoma." American Journal of Clinical Oncology, Dec. 2012, vol. 35, No. 6, pp. 606-611.
Merhavi-Shoham, et al., "Genetically modulating T-cell function to target cancer", Seminars in Cancer Biology 2012, vol. 22 pp. 14-22.
Erfani, et al., "Increase of regulatory T cells in metastatic stage and CTLA-4 over expression in lymphocytes of patients with non-small cell lung cancer (NSCLC)", Lung Cancer 2012, vol. 77, pp. 306-311.
Langowski, et al., "Swords into plowshares: IL-23 repurposes tumor immune surveillance", Trends Immunol 2007, vol. 28, No. 5, pp. 207-212.
Sica, A, et al., "Cancer related inflammation: the macrophage connection", Cancer Letters 2008, vol. 264, pp. 204-215.
Gruber, et al., "Relationship between circulating tumor cells and peripheral T-cells in patients with primary breast cancer", Anticancer Research 2013, vol. 33, pp. 2233-2238.
Santegoets, SJ. et al., "T cell profiling reveals high CD4+CTLA-4+ T cell frequency as dominant predictor for survival after prostate GVAX/ipilimumab treatment", Cancer Immunology Immunotherapy: CII 2013, vol. 62, pp. 245-256.
Zhang, J. et al., "Preoperative lymphocyte count is a favorable prognostic factor of disease-free survival in non-small-cell lung cancer", Med Oncol 2013, vol. 30, pp. 352.
Jotereau, F. et al., "Adoptive transfer with high-affinity TCR to treat human solid tumors: how to improve the feasibility?", Targeted Oncology 2012, vol. 7, p. 3-14.
Halama et al, "Quantification of Prognostic Immune Cell Markers in Colorectal Cancer Using Whole Slide Imaging Tumor Maps", Analytical and Quantitative Cytology and Histology, vol. 32, pp. 333-340, 2010.
John Burczak, Ph.D, "Spotlight-on-cancer-diagnostic-tech-what-is-ge-clarients-multiplexing", GE Reports, Sep. 15, 2011.
Pages, Franck et al. "Tumor-infiltrating lymphocytes as a prognosis biomarker: in situ immune response in colorectal cancer", 1st European Symposium of BioPathology Jun. 14-15, 2012, Paris France.

\* cited by examiner

QUANTITATIVE IN SITU CHARACTERIZATION OF BIOLOGICAL SAMPLES

BACKGROUND

The subject matter disclosed herein relates to immune profiling of biological samples. More particularly, the disclosed subject matter relates to determining one or more immune cell characteristics of the biological sample, including a distribution, type and/or location of immune cells within the sample.

Various methods may be used in biology and in medicine to observe different targets in a biological sample. For example, analysis of proteins in histological sections and other cytological preparations may be performed using the techniques of histochemistry, immunohistochemistry (IHC), or immunofluorescence.

Many of the current techniques may detect a presence or concentration of biological targets without maintaining information about original location of those targets within the sample. For example, certain techniques involve processing the sample in such a way that the original location information is lost. Other techniques may involve assessing only a limited number of targets from a given sample Further analysis of targets may require additional sampling from the source (repeated biopsy) thereby limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

BRIEF DESCRIPTION

In one embodiment, a method for determining infiltration of multiple immune cell populations in a biological sample is provided. The method includes applying a plurality of probes to a biological sample in a sequential manner; acquiring image data of the biological sample representative of the respective plurality of probes bound to a respective plurality of targets in the biological sample, wherein at least one of the plurality of probes comprises an epithelium probe, a membrane probe, a cytoplasm probe, or nuclear probe specific for a cell nucleus and wherein at least one of the plurality of probes comprises an immune probe specific for an immune marker; segmenting epithelial and stromal regions of the sample to identify single cells within each region, wherein identifying individual cells in the epithelial region or the stromal region comprises using image data representative of the epithelium probe, the membrane probe, the cytoplasm probe, or the nuclear probe and wherein identification of cells in the stromal region comprises segmenting the epithelial region of the sample to generate an epithelial mask and classifying regions not contained within the epithelial mask as one or more of the stromal region or background; identifying immune cells among the single cells based on the image data representative of the immune marker, wherein identifying comprises reclassifying single cells in the sample as immune cells based on a signal from the immune probe above a threshold value; and determining a distribution, location, and type of a plurality of immune cells in the biological sample.

In another embodiment, a system for assessing a biological sample from a patient is provided. The system includes a memory storing instructions for: acquiring image data of a biological sample representative of a respective plurality of probes bound to a respective plurality of targets in the biological sample, wherein at least one of the plurality of probes comprises an epithelium probe, a membrane probe, a cytoplasm probe, or nuclear probe specific for a cell nucleus and wherein at least one of the plurality of probes comprises an immune probe specific for an immune marker; segmenting epithelial and stromal regions of the sample to identify single cells within each region, wherein identifying individual cells in the epithelial region or the stromal region comprises using image data representative of the epithelium probe, the membrane probe, the cytoplasm probe, or the nuclear probe and wherein identification of cells in the stromal region comprises segmenting the epithelial region of the sample to generate an epithelial mask and classifying regions not contained within the epithelial mask as one or more of the stromal region or background; identifying immune cells among the single cells based on the image data representative of the immune marker, wherein identifying comprises reclassifying single cells in the sample as immune cells based on a signal from the immune probe above a threshold value; and determining a distribution, location, and type of a plurality of immune cells in the biological sample. The system also includes a processor configured to execute the instructions.

In another embodiment, a system for assessing a biological sample from a patient is provided. The system includes a memory storing instructions for: acquiring image data of a biological sample representative of a respective plurality of probes bound to a respective plurality of targets in the biological sample, wherein at least one of the plurality of probes comprises a nuclear probe specific for a cell nucleus and wherein at least one of the plurality of probes comprises an immune probe specific for an immune marker; segmenting epithelial and stromal regions of the sample to identify single cells within each region, wherein identifying individual cells in the epithelial region or the stromal region comprises using image data representative of the nuclear probe and wherein identification of cells in the stromal region comprises segmenting the epithelial region of the sample to generate an epithelial mask; and identifying immune cells in the epithelial region among the single cells based on the image data representative of the immune marker, wherein identifying comprises reclassifying single cells in the epithelial region as immune cells based on a signal from the immune probe above a threshold value; The system also includes a processor configured to execute the instructions.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
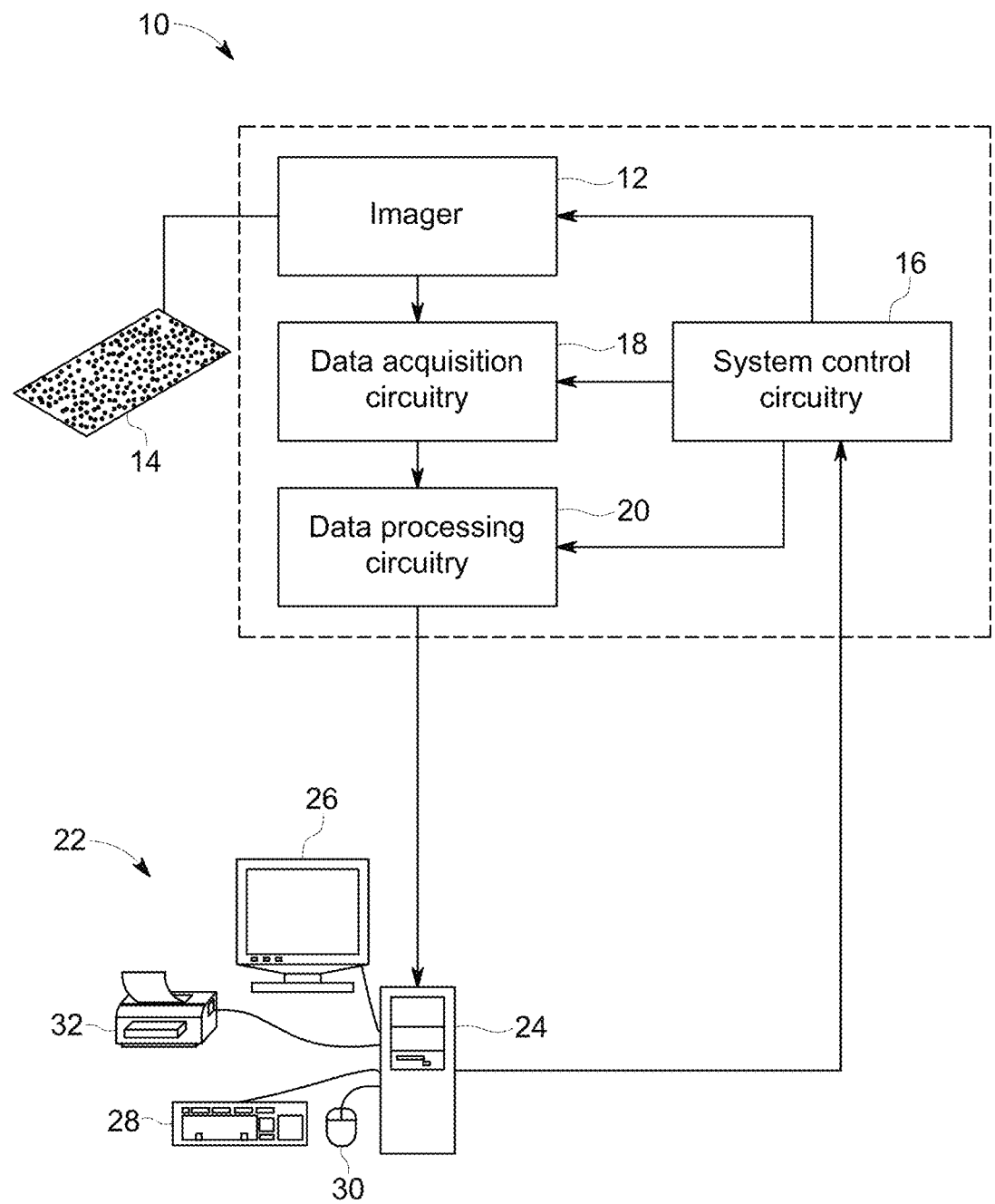
FIG. 1 is a block diagram illustrating an embodiment of a system for assessing a biological sample according to an embodiment of the present disclosure.

The present disclosure relates to detecting cell distribution and quantification from biological samples. In one embodiment, the disclosed embodiments may be used to assess a cell profile of a biological sample. For example, such techniques may be used to assess the sample and based on the assessment, diagnose a particular clinical condition (e.g., presence or absence of a disease or condition), provide a prognosis, direct therapy, and/or determine a cell distribution profile for a clinical condition based on the distribution and location of cells and/or cell types in the sample and their associated microenvironments.

In a particular example the disclosed embodiments may be used to determine an immune cell biodistribution in a Tumor microenvironment (TME). A TME includes an assortment of cells and tissues of distinct lineage, including mutant tumor cells, blood vessels, lymph vasculature, fibroblasts, smooth muscle, neurons, glial cells, diverse immune cells, and extracellular matrix proteins. The immune cell composition, functional orientation, density, and location of infiltration may influence the clinical outcome of the patients. For instance, CD4 T-lymphocytes may adopt different phenotypes with different prognostic implications in diverse cancers and high level tumor infiltration by TH1-polarized CD4 T-lymphocytes is often associated with a favorable prognosis. In contrast, high abundance of TH2, TH17 or T-regulatory polarized cells is often associated with a negative prognosis. CD8+ cytotoxic T-lymphocytes are commonly found in association with tumor antagonistic functions and therefore predictive of positive disease prognosis. Importantly, the definition of CD4 T-lymphocyte polarization status can only be achieved by establishing the presence or absence of expression of a constellation of multiple molecules in the same cells from the same sample.

Hierarchical polarization is also seen in innate immune cells. For example, at least two phenotypes of macrophages (M1 and M2) have been identified. Neutrophils have recently been associated with similar dual polarization (N1 and N2)13. M1 and N1 polarized cells are tumor antagonistic may be associated with improved prognosis. M2 and N2 are tumor promoting, and may be associated with a poor prognosis. Like CD4 T-lymphocytes, neutrophil and macrophage polarization can only be defined by the measuring the expression of a constellation of molecules reflecting differential activities amongst morphologically similar cells.

Accordingly, identification of a total number of immune cells may not provide a complete picture of a patient's prognosis when certain types of immune cells are tumor promoting while other types are tumor antagonistic. In contrast, a distribution of particular types of immune cells, e.g., relative to one another and numbers of cells and types of cells in different locations such as stromal vs. epithelial or in proximity to tumor area residence may provide a more accurate assessment of cancer progression.

Provided herein are techniques that identify a type, distribution, and location of a plurality of cells and/or cell biomarkers on a single tissue section profile. For example, the distribution of immune cells between epithelial and non-epithelial regions of a sample may be determined. In turn, the profile of the immune biodistribution may be used to evaluate prognostic signatures in human cancers and disease tissue. Further, the location-specific information (e.g., epithelial or stromal) obtained by the protein multiplexing combined with the biomarker information on a single tissue sample can provide information regarding prognosis.

The present techniques may be performed in situ, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed. In situ techniques, such as those provided herein, permit assessment of cell profiles in a particular microenvironment. Such methods may be in contrast to techniques in which the cell microenvironments are disrupted to conduct analysis. Further, the techniques facilitate cell level tissue loss.

The present techniques provide systems and methods for image analysis. In certain embodiments, it is envisioned that the present techniques may be used in conjunction with previously acquired images, for example, digitally stored images, in retrospective studies. In other embodiments, the images may be acquired from a physical sample. In such embodiments, the present techniques may be used in conjunction with an image acquisition system. An exemplary imaging system 10 capable of operating in accordance with the present technique is depicted in FIG. 1. Generally, the imaging system 10 includes an imager 12 that detects signals and converts the signals to data that may be processed by downstream processors. The imager 12 may operate in accordance with various physical principles for creating the image data and may include a fluorescent microscope, a bright field microscope, or devices adapted for suitable imaging modalities. In general, however, the imager 12 creates image data indicative of a biological sample including a population of cells 14, shown here as being multiple samples on a tissue micro array, either in a conventional medium, such as photographic film, or in a digital medium. As used herein, the term "biological material" or "biological sample" refers to material obtained from, or located in, a biological subject, including biological tissue or fluid obtained from a subject. Such samples can be, but are not limited to, body fluid (e.g., blood, blood plasma, serum, or urine), organs, tissues, biopsies, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, an antigen from a biological fluid (e.g., blood or urine). The biological samples may be imaged as part of a slide.

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic, electronic, or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquisition image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple wells of a multi-well plate). The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the computer 24 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the computer 24. The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images. Thus, the image processing, segmenting, and/or enhancement techniques described herein may be carried out remotely from the imaging system, as on completely separate and independent workstations that access the image data, either raw, processed or partially processed and perform the steps and functions described herein to improve the image output or to provide additional types of outputs (e.g., raw data, intensity values, cell profiles).

Figure 2:
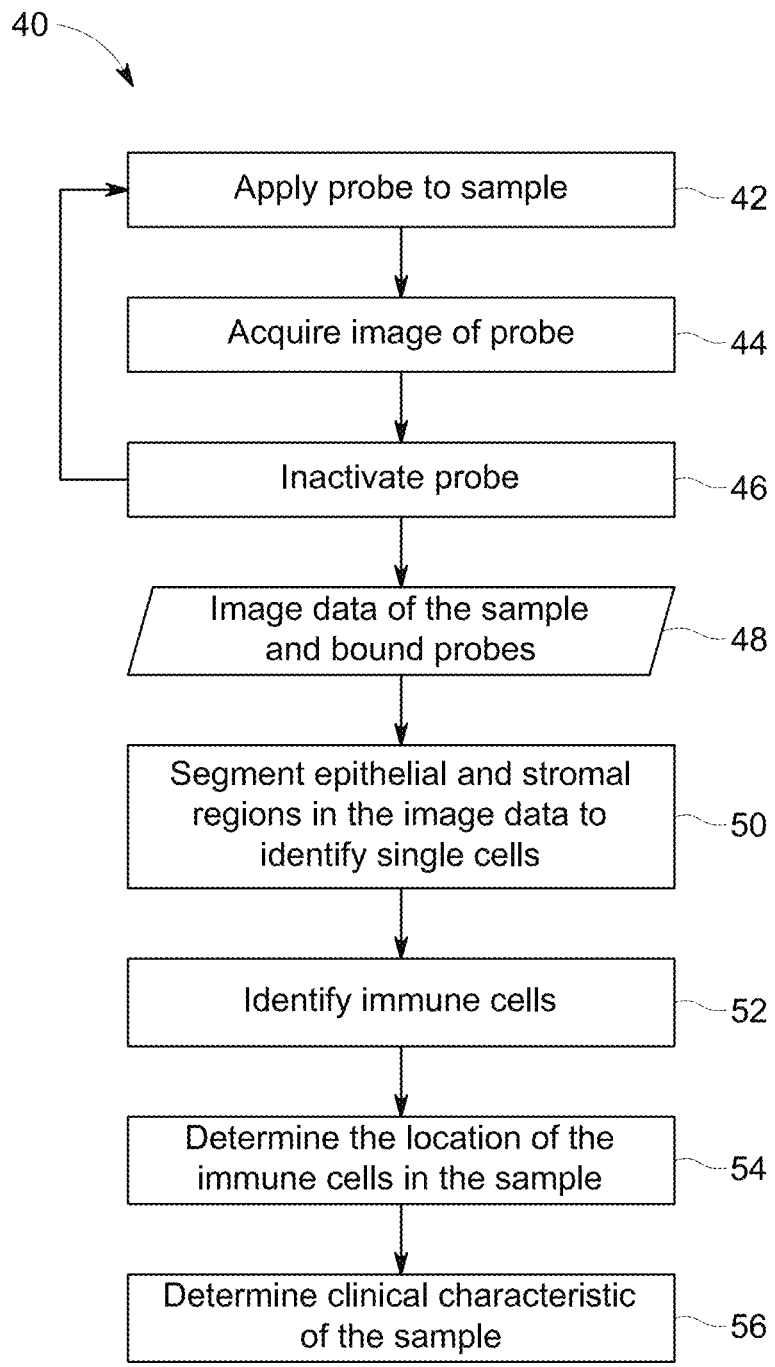
FIG. 2 is a flow diagram of a quantitative in situ biological sample characterization according to an embodiment of the present disclosure.

The computer analysis method 40 used to analyze images is shown in FIG. 2. It should be understood that the method 40 may also be used with stored images that are retrospectively analyzed. Typically, one or more images of the same sample may be obtained or provided. In step 42, the biological sample is prepared by applying a plurality of probes. In one embodiment, the probes are applied in a sequential manner. The probes may include probes for identifying cellular regions such as the cell membrane, cytoplasm and nuclei. In such an embodiment, a mask of the stromal region may be generated, and using curvature and geometry based segmentation (step 44), the image of the compartment marker or markers is segmented. For example, the membrane and nuclear regions of a given tumor region may be demarcated. The cytoplasm may be designated as the area between the membrane and nucleus or within the membrane space. Any number and type of morphological markers for segmentation may be used.

FIG. 2 is a flow diagram of one embodiment of a technique 40 for assessing a biological sample as provided herein. At step 42, one or more probes is applied to the biological sample 14. The probe may be applied as part of a multi-molecular, multiplexing imaging technology such as the GE Healthcare MultiOmyx™ platform. For example, the probe may be applied and an image maybe acquired at step 44 by the imaging system 10. The image may be in the form of image data that is representative of the probe bound to the target of interest on the sample. Rather than use a separate slide or section to then assess a second probe relative to the first probe, e.g., via image registration techniques on the acquired images, the probe may be inactivated, e.g., via a chemical inactivation, at step 46 before application of a subsequent second probe. The method 40 then returns to step 42 for sequential probe application, image acquisition, and probe inactivation until all of the desired probes have been applied. In particular embodiments, the disclosed techniques may be used in conjunction with any number of desired probes, including 2, 3, 4, 5, 6, 7, 8, 9, 10 or more probes per sample. Accordingly, the acquired image data 48 represents a plurality of images, and individual images within the data may be associated with a detected intensity of a particular probe. In one embodiment, the sequential probe imaging may be performed as disclosed in U.S. Pat. No. 7,629,125, which is incorporated by reference herein in its entirety for all purposes. During the sample handling, certain quality control steps may be taken to account for marker staining variability. For example, replicates may be stained.

At step 50, the image data 48 is segmented to identify individual cells. For example, for a sample including a tumor, the sample may be segmented into epithelial and stromal regions, and individual cells within the epithelial region and the stromal region may also be identified. In a particular embodiment, the probes may include probes to immune markers as well as probes specific for segmenting markers and morphological markers, e.g., epithelium probes, membrane probes, cytoplasmic probes, and/or nuclear probes. Accordingly, the image data 48 may include information to facilitate segmenting as well as information to identify immune cell types. The method 40 may include one or more quality control features to exclude poorly stained markers or poorly segmented spots. Further, the identification of individual cells may include quality control features such as thresholds to exclude certain cells based on staining or signal quality. Once the individual cells are identified, cells that are immune cells, or any other type of cell, may be identified using the image data 48 of the bound probes specific for immune cell markers. For example, while a tumor cell sample may be mostly made up of epithelial cells, there may be some immune cells that have been recruited to the area. Based on the type of tumor and the stage of progress, certain immune cells may infiltrate the epithelial regions of the tumor. Accordingly, by determining the location of the immune cells at step 54 (e.g. epithelial vs. stromal), along with the specific types of cells in the sample at step 52 (e.g., B cell, T cell, neutrophils, macrophages) as well as the relative numbers of immune cells of each type, the method 40 may determine a clinical characteristic of the sample at step 56.

The method 40 may also provide an output related to the clinical characteristic, for example via a display associated with the system 10 or stored in a memory of the system 10. The output may include one or more of a histogram, boxplot, density plot, violin plots, or numerical values corresponding to such plots. In one embodiment, the output may be an immune profile of the sample. The immune profile may include a total number of all immune cells in the sample and/or in the epithelial and stromal regions, a total number of each type of immune cell in the sample and/or in the epithelial and stromal regions, or a histogram of the immune cell types in the sample and/or in the epithelial and stromal regions. Further, for each type of immune cell that includes subtypes (e.g., N1 and N2 cells), the immune profile may also include distribution and location information for immune cell subtypes. In addition to identification of immune cells as being stromal or epithelial, the present techniques may also assess location relative to a tumor edge or infiltration into the tumor. Such assessment may be made using detected borders or other features via appropriate segmentation techniques. In one embodiment, the output may be a single marker expression average for epithelial, stromal, and whole image regions. The output may also include metrics such as skewness, a standard deviation, or coefficient of variation of the marker distribution. In another embodiment, the output may also include a percentage of positive cells in stromal, epithelial, and whole image regions that may also include additions of manual data. For example, once the image is segmented to identify cells and to identify marker distribution, an end user may then perform a manual quality check and add or remove cells.

In one embodiment, the technique may be used to assess an unknown clinical condition by comparing the immune profile of a biological condition to one or more reference profiles of known clinical conditions. The reference profiles may be stored in the memory of the system 10. In such an example, the immune profile may be used for providing a diagnosis. In another embodiment, the immune profile may be used to determine if a therapy is working. For example, certain therapies may be designed to recruit immune cells to tumor tissues, e.g., T cell therapy. Accordingly, immune profiles taken before and after treatment may be used to determine if the therapy is working. In another embodiment, the immune profile may be used to assess if a particular type of therapy is likely to be successful.

Further, the immune profile may also provide information on linked markers to identify particular clinical conditions. For example, certain markers may be co-localized in particular disease states. In addition, certain markers may be assessed in groups for quality or confidence metrics. In one embodiment, a cell type may be identified by multiple marker profiles using clustering.

Figure 3:
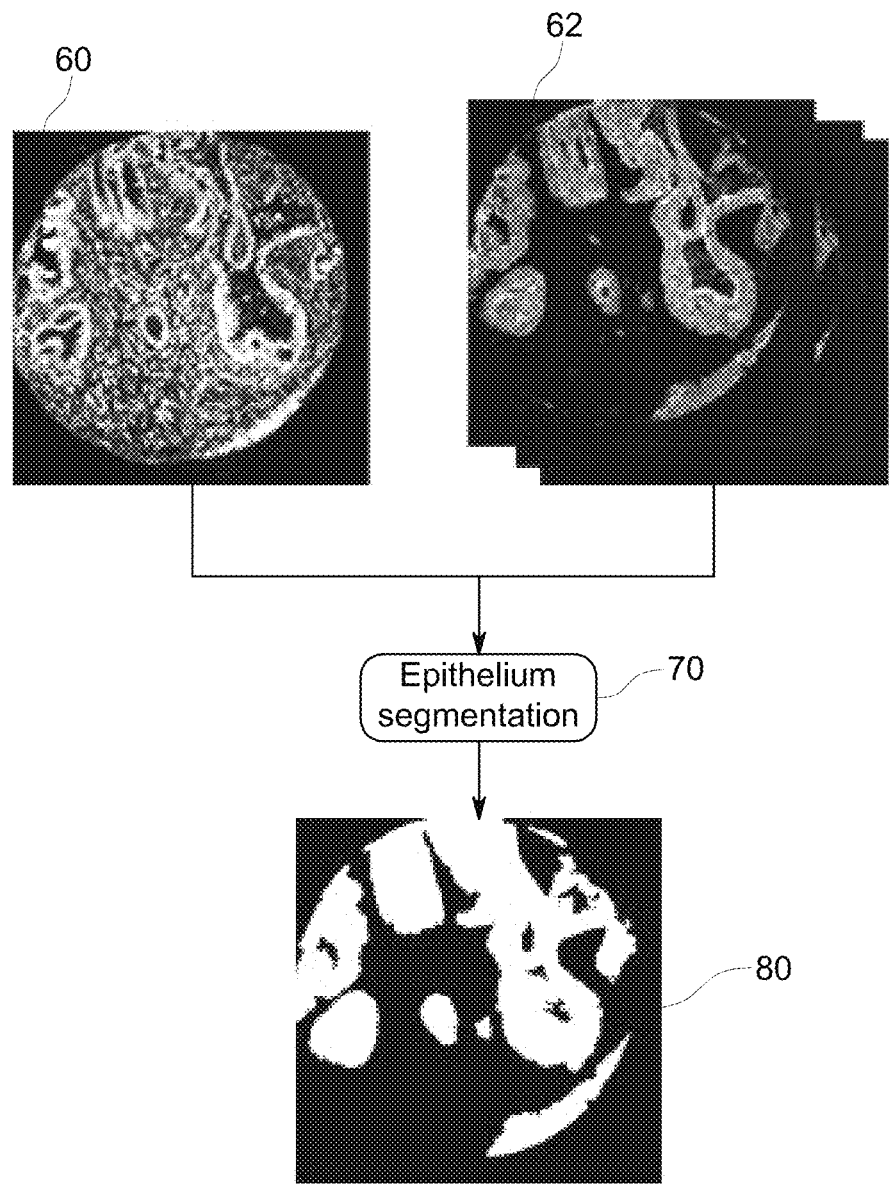
FIG. 3 is an input to an epithelial segmentation.
Figure 4:
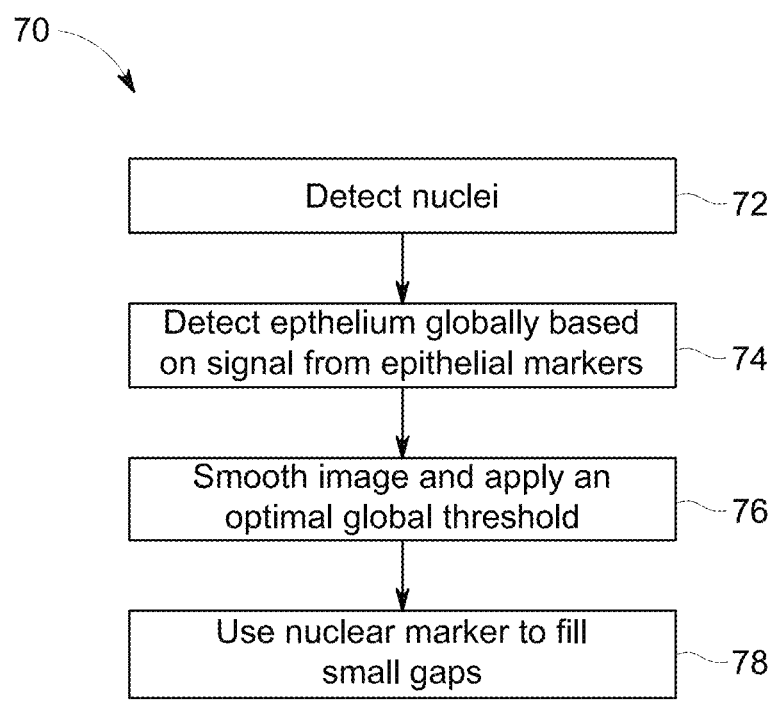
FIG. 4 is a flow diagram of an epithelial segmentation according to an embodiment of the present disclosure.

Turning to the segmentation of the image data, stromal-epithelial segmentation may include epithelium—stroma segmentation tissue classification, stroma cell segmentation and quantification, and stroma cell phenotype clustering. Stroma segmentation may be performed by using the following markers: i) DAPI (nuclei) marker and ii) a number epithelium markers (e.g., one or more epithelium marker). FIG. 3 shows an image input to a segmenting algorithm of DAPI marker 60 and epithelium markers 62. An implementation of the epithelium segmentation algorithm 70 is shown in FIG. 4. First, nuclei are detected from the DAPI marker at step 72. Then, epithelium tissue is globally detected from the epithelium markers at step 74. If more than one epithelium marker is provided, the information from the multiple markers will be fused to produce a super-epithelium image. Then, the epithelium tissue is detected by smoothing the image and automatically applying an optimal global threshold at step 76. Finally, the detected DAPI is utilized to fill-up small gaps from the super-epithelium marker at step 78 to yield a segmented image 80 (FIG. 3).

The stromal segmentation may be performed using probabilistic-based methods, such as those provided in U.S. Pat. No. 8,300,938 to Ali Can et al., whereas the epithelium cell segmentation may be performed as the method provided in the U.S. patent application entitled "Systems And Methods For Multiplexed Biomarker Quantitation Using Single Cell Segmentation On Sequentially Stained Tissue", Ser. No. 13/865,036 filed Apr. 17, 2013. Two-class clustering may be used to differentiate between cells with low and high DAPI signal using intensity followed by a log transform of the intensity. Alternatively, detected cells may be assessed by estimating global thresholds from the mean intensity value of the cell to identify the positive DAPI nuclei in the stroma. For cell phenotype clustering, at least two methods can be used: a) unsupervised, moments and percentile derived thresholds, and b) supervised methods. For the supervised method, a small number of test case images (5-10% of all images) are randomly selected. In each image, small regions are selected and marked either positive or negative in an image visualization and quantitation software package. The biomarker staining intensity in the positive regions form a distribution of signal and the staining intensity in the negative regions form a distribution of background. To derive the cutoffs the following steps were used:
1. For each marker, on each slide, get x=median (for negative regions)+3* Median absolute deviance (MAD) (for negative regions)
2. For each marker, on each slide, get y=min(for positive regions)
3. Cutoff=max (x, y), if x/y is not available, take y/x.

Figure 5:
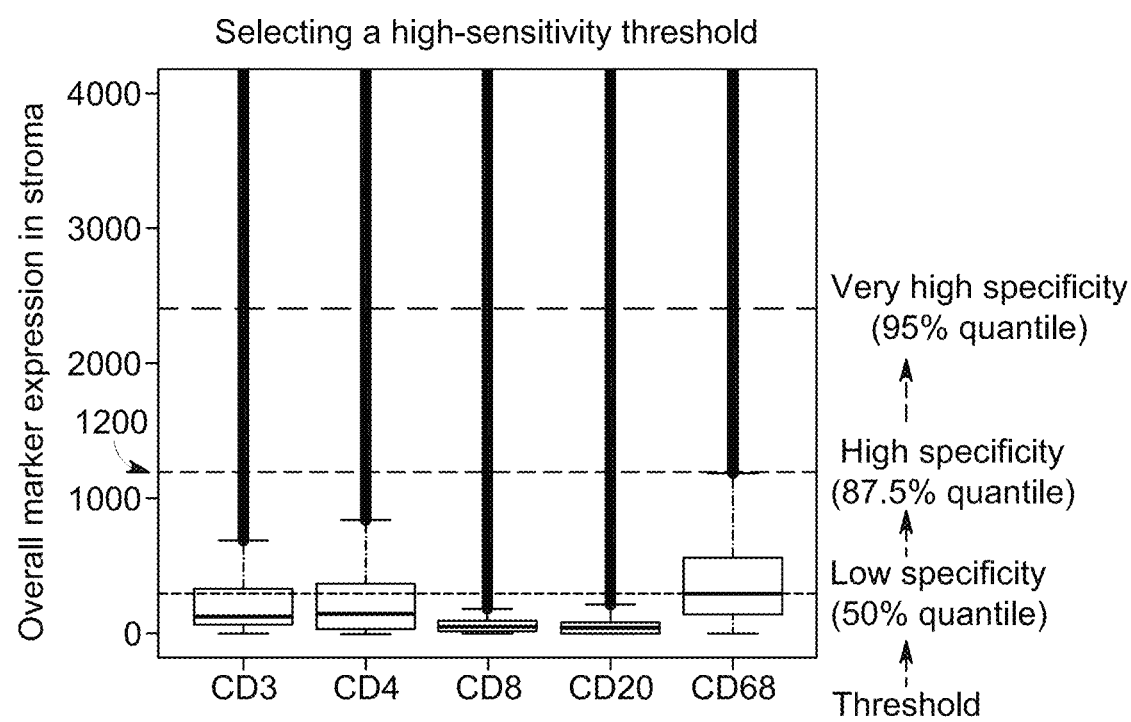
FIG. 5 is a plot of sensitivity thresholds for immune cell marker expression.

For one unsupervised method, two thresholds were considered: low data threshold (representing high sensitivity) and high data threshold (representing high specificity). FIG. 5 represents boxplot analysis of immune cell marker expression in stroma yielding high specificity threshold. In another unsupervised method, moments and hotspots of the single cell data are used to estimate the immune cell distributions in the epithelial and stromal regions, as well as in the total image. Moments are defined as median, mean, standard deviation, skewness, and coefficient of variation. Hotspots are defined as the proportion of cells in the region to be analyzed that exceed some population derived percentile (set to 90% in the described CRC analysis). These analyses give a continuous measurement of different immune cell features.

In one embodiment, the epithelial mask is first generated, and the edge of the mask determined. This edge represents the border of tumor to stroma and the cartesian positions encompassing this edge are used to generate distance metrics of immune cells to tumor border. The distance from this point can be then fixed to an arbitrary distance to cover multiple cell widths (for example 50 microns) and density of the cells within this distance and relative distribution of subtypes determined

EXAMPLES

Multiplexing technology from GE was applied on slides consisting of colon, lung or melanoma tissue microarray (TMA) to map multiple protein expressions of non-neoplastic cells (panel of immune biomarkers and segmentation markers) in the tumor microenvironment. Multiple targets were applied on a single tissue section.

Lung TMA: Tristar 69571118 NSCLC prognosis tissue array was used which had tissues from 144 European male smokers along with patient information. Slides (#1167) containing various clinic pathological information like histologic types, stage, age, sex, predominantly from squamous and adenocarcinoma were selected for immune profiling. Melanoma TMA: Pantomics MEL961 Melanoma tissue array contained 48 cases of primary and metastatic cancer in duplicates. Colorectal Cancer TMA: Colorectal cancer tissue microarrays were provided by Clarient INC. The colorectal cancer cohort was collected from the Clearview Cancer Institute of Huntsville, Ala. from 1993 until 2002, with 747 patient tumor samples collected as paraffin embedded specimens. The median follow-up time of patients in this cohort is 4.1 years, with a maximum of over ten years. Stage 2 patients were 38% of this cohort, stage 1 and 2 combined were 65% of total patients.

TMA scan plan: FOV were chosen (1-4 spots) from each tissue core of TMA and imaged under 20× objective in Olympus scope. Lung TMA: The multi-round staining for this study consisted of 8 immune biomarkers (CD3, CD4, CD8, CD20, CD68, CD163, CD11c, FoxP3), one stromal marker (Vimentin) and 4 segmentation markers for downstream analysis. Melanoma TMA was stained with 8 immune markers (CD3, CD4, CD8, CD20, CD68, CD163, CD11c, FoxP3), one stromal marker (Vimentin) and 3 segmentation marker for downstream analysis. Colorectal Cancer TMA: this TMA was stained with 7 immune markers (CD3, CD8, Claudin1, CD68, CD163, CD20, CD79) for immune cell profiling, 4 stromal cell markers (CD31, SMA, Collagen IV, Fibronectin) and 3 segmentation markers for downstream analysis.

Two large tissues whole mount tissue section from Pantomics were used (a) Breast cancer (b) colon cancer. FFPE slides were baked at 65 C for 1 hour. Slides then went through the process of de-paraffinization with Histochoice clearing agent (Amresco), rehydration by decreasing EtOH concentration washes followed by antigen retrieval process. An in house 2-step antigen retrieval method was used. Slides were incubated in PBS with 0.3% Triton X-100 for 10 minutes at ambient temperature before blocking against non-specific binding with 10% donkey serum in 3% BSA: 1×PBS overnight at 4 C. Slides were washed sequentially in PBS, PBS-TritonX-100, and then PBS again for 10 minutes each with agitation.

All TMA slides were stained and scanned under Olympus microscope. A scan plan was generated for each slide.

Lung TMA: The multi-round staining for this study consisted of 8 immune biomarkers (T cell, B cell, macrophage and DC), 4 segmentation markers, 1 stromal marker and 1 blood vessel marker. The tissue was bleached and imaged after every round of staining for first 5 rounds. Cy3 and Cy5 direct conjugate antibody pairs were used in each round as shown in Table 1.

TABLE 1

Cell types in Lung Cancer Analysis

| Marker | Cell/feature type |
|---|---|
| CD3 | all T-lymphocytes |
| CD4 | Helper T-lymphocytes |
| CD8 | cytotoxic T-lymphocytes |
| FOXP3 | T-regulatory lymphocytes |
| CD20 | B-lymphocytes |
| Claudin1 | neutrophils |
| CD68 | macrophages |
| CD163 | macrophages |
| ALDH1 | variable cell types |
| CD31 | Endothelial cells |
| Vimentin | mesenchymal cells |

Melanoma TMA: This TMA was stained with 8 immune markers, 1 blood vessel markers and 3 segmentation markers. The antibody round are shown in Table 2.

TABLE 2

Cell types in Melanoma Analysis

| Marker | Cell/feature type |
|---|---|
| CD3 | all T-lymphocytes |
| CD4 | Helper T-lymphocytes |
| CD8 | cytotoxic T-lymphocytes |
| FOXP3 | T-regulatory lymphocytes |
| CD20 | B-lymphocytes |
| CD11c | dendritic cells |
| Claudin1 | neutrophils |
| CD68 | macrophages |
| CD163 | macrophages |
| ALDH1 | variable cell types |
| CD31 | Endothelial cells |

Colorectal Cancer TMAs: Three CRC TMAs were stained with 16 markers relevant to immune cell profiling in human tissues: 7 immune cell markers (CD3, CD8, Claudin1, CD68, CD163, CD20, CD79); 4 stromal cell markers (CD31, SMA, Collagen IV, Fibronectin); 4 segmentation markers (Na+K+ ATPase, Ribosomal Protein S6, pan-Cytokeratin, and DAPI); ALDH1 is a functional marker that is expressed by varying cell types including immune cells (Table 3).

TABLE 3

Cell types in Colorectal Cancer Analysis.

| Marker | Cell/feature type |
|---|---|
| CD3 | all T-lymphocytes |
| CD8 | cytotoxic T-lymphocytes |
| CD2O | B-lymphocytes |
| Claudin1 | neutrophils |
| CD68 | macrophages |
| CD163 | macrophages |
| ALDH1 | variable cell types |
| SMA | smooth muscle cells |
| Fibronectin | Extracellular matrix |
| Collagen 4 | Extracellular matrix |
| CD31 | Endothelial cells |

For indirect detection of bound primary antibodies, species-specific Cy3-or-Cy5-conjugated donkey secondary antibodies were obtained from Jackson ImmunoResearch and used at a dilution of 1:250. Primary antibodies were directly conjugated to either Cy3-or-Cy5 (GE Healthcare) or purchased as the Cy3 conjugate (see above). If not supplied in purified form, Protein A or G HP SpinTrap or HiTrap columns (GE Healthcare) were used following the manufacturer's protocols to purify the antibody prior to conjugation. After purification, the concentration was adjusted to 0.5-1.0 mg/mL and the pH was adjusted to 8.2-9.0 with 1.0 M sodium bicarbonate to a final bicarbonate concentration of 0.1 M. A small amount of N-hydroxysuccinimidyl (NHS)-ester dye was dissolved in anhydrous DMSO and the concentration was determined by measuring the absorbance of a 1:250 dilution of dye stock in 1×PBS at the appropriate wavelength on a ND-1000 spectrophotometer (NanoDrop Technologies). The appropriate amount of reconstituted NHS-dye was added to each reaction to yield a ratio of 2, 4, or 6 dye molecules per antibody and the reaction was left in the dark at room temperature. After 90 minutes, the reactions were terminated, buffer exchanged and purified using Zeba desalting columns (Pierce) that had been equilibrated with 1×PBS buffer. The conjugation efficiency (dyes/antibody) was measured on a ND-1000 spectrophotometer using the appropriate absorbance measurements and the following equations (assuming a 1 cm. path length in spectrophotometer). Dye concentration correction factors were included to measure [Ab]:

$$[Ab](uM)=(A280-(0.08*A550)/0.210 \text{ for Cy3}$$

$$[Ab](uM)=(A280-(0.05*A650)/0.210 \text{ for Cy5}$$

$$[Cy3](uM)=A550/0.15$$

$$[Cy5](uM)=A650/0.25$$

$$D/P=Dye(uM)/Ab(uM)$$

Solutions were stabilized with BSA (0.2%, final concentration) and azide (0.09%, final concentration). Fluorescence intensities were collected for direct conjugates by preparing 50 nM antibody solutions and reading intensities on a BioRad FX Imager using the appropriate filter sets. Antibody dilutions for staining tissue were determined empirically for each antibody.

FFPE tissue samples or tissue arrays were baked at 65° C. for 1 hour. Slides were de-paraffinized with Histochoice clearing agent (Amresco), rehydrated by decreasing EtOH concentration washes, and then processed for antigen retrieval. A 2-step antigen retrieval method was developed specifically for multiplexing with FFPE tissues which allowed for the use of antibodies with different antigen retrieval conditions to be used together on the same samples. Samples were then incubated in PBS with 0.3% Triton X-100 for 10 minutes at ambient temperature before blocking against non-specific binding with 10% donkey serum, 3% BSA in 1×PBS for 45 minutes at room temperature. Primary antibodies were diluted to optimized concentrations (typical range 0.1-10 µg/ml) and applied for 1 hour at room temperature or O/N at 4° C. in PBS/3% BSA. Samples were then washed sequentially in PBS, PBS-TritonX-100, and then PBS again for 10 minutes each with agitation. In the case of secondary antibody detection, samples were incubated with primary antibody species-specific secondary Donkey IgG conjugated to either Cy3 or Cy5. Slides were then washed as above and stained in DAPI (10µ/ml) for 5 minutes, rinsed again in PBS, then mounted with antifade media for analysis. For the dye cycling process, following image acquisition, coverslips were floated away from the samples by soaking the slides in PBS at room temperature.

The general dye inactivation protocol used with tissues or cells was as follows: After image acquisition from a round of staining, slides were immersed in PBS to allow the cover slip to float off the slide. Samples were further washed in PBS and PBS/0.3% TritonX-100 and then dye inactivation was performed as previously described in U.S. Pat. No. 7,741,045, which is incorporated by reference in its entirety herein. Briefly, slides were immersed in an alkaline solution containing $H_2O_2$ for 15 minutes with gentle agitation at room temperature. After 15 minutes, the slide was washed again with PBS. The sample was then either imaged to check the efficacy of the dye inactivation or re-stained with another round of antibodies followed by another round of image acquisition.

Antibodies were selected on the basis of 1) staining specificity and sensitivity in indirect immunofluorescence, 2) compatibility with the two-step antigen retrieval method described above, 3) resilience in 1, 5 and 10 rounds of dye inactivation chemistry. Specificity tests included (where applicable to the antibody) immunogen peptide blocking prior to incubation with tissue, drug-treated fixed cell lines, fixed cell lines with gene amplification or deletion, phosphatase treatment of samples to verify phosphospecificity, and visual inspection of expected localization patterns. Fluorescent dyes were conjugated to the primary antibody at several initial dye substitution ratios and specificity of each conjugate was verified and sensitivity was compared to levels found in previous experiments.

Images were obtained using an Olympus IX81 inverted fluorescence microscopy platform. The system was equipped with Prior illuminator—LumenPro 220 for florescence excitation, and an H117 ProScan™ Flat Top Inverted Microscope stage from Prior. DAPI, FITC (used for Cy2 imaging), Cy3, and Cy5 filters were from Semrock and matched to specifications for the equivalent filters used on the Zeiss platform. Images were acquired at 20× magnification using Olympus USPlanApo 20× 0.75 NA objective and QImaging Retiga 4000DC Cooled CCD camera and saved as 12-bit gray-scale TIFF images.

The multiplexed experiments were set up such that nuclear (DAPI) images were acquired at each step. The nuclear images in each step were then registered to the nuclear images of a reference (typically the first) step, and images of all other channels were shifted accordingly. The rigid registration, involving only translation and rotation parameters, was performed in two steps. First, global translation parameters (no rotation) were computed using normalized correlation in the Fourrier domain. Normalized correlation guarantees a close-to-optimal solution even if the misalignment of the tissues is large from one step to another, and the computation was performed in the Fourrier domain for speed benefits. In the second step which involves rotation, normalized mutual information metric was used for the registration, starting from the initial translation obtained by Fourrier transform. Mutual information was robust to intensity differences between images.

Autofluorescence was removed with an image of the unstained sample is acquired in addition to the stained image. The unstained and stained images were normalized with respect to their exposure times and the dark pixel value (pixel intensity value at zero exposure time). Each normalized autofluorescence image was then subtracted from the corresponding normalized stained image.

Following multiplexing, the data went through the following image processing steps. (1) Slide normalization (2) image registration (3) autofluorescence removal (4) single cell segmentation (5) image visualization QC [to check for segmentation flaws or marker stain flaws] (6) data visualization QC [to check for global marker distribution] and (7) stromal analysis quantification Stromal Analysis: To identify stromal region, first epithelial region of the cancerous tissue was segmented, followed by a generalized wavelet-based nucleus segmentation detection of the stromal region. For cell phenotype clustering classification, two methods were used: a) unsupervised, moments and percentile derived thresholds, and b) supervised methods.

Image visualization was performed after the images were processed through server and uploaded on GE proprietary visualization software where co registered merged images for multiple proteins were generated. Cell network, protein co-localization, spatial resolution of various cell types and features in tumor microenvironment were visualized, recorded and presented.

Threshold selection: A threshold of 1200 was used for all 5 immune biomarkers (CD3, CD4, CD8, CD20 and CD68) to increase specificity in the lung cancer TMA. A higher threshold will select immune cell marker positive cells with higher confidence. The value 1200 was chosen based on the box-plot analysis of overall immune marker expression in stromal tissue across all cores (FIG.-5). Specifically, the quantiles for each immune marker was computed and the expression value greater than or equal to 1200 corresponding to the 87.5% quantile was selected. Higher or lower specificity may be selected, and this threshold value may change correspondingly (for example, 2400 for ~95% quantile and 300 for 50% quantile, as shown in FIG. 5).

Figure 6:
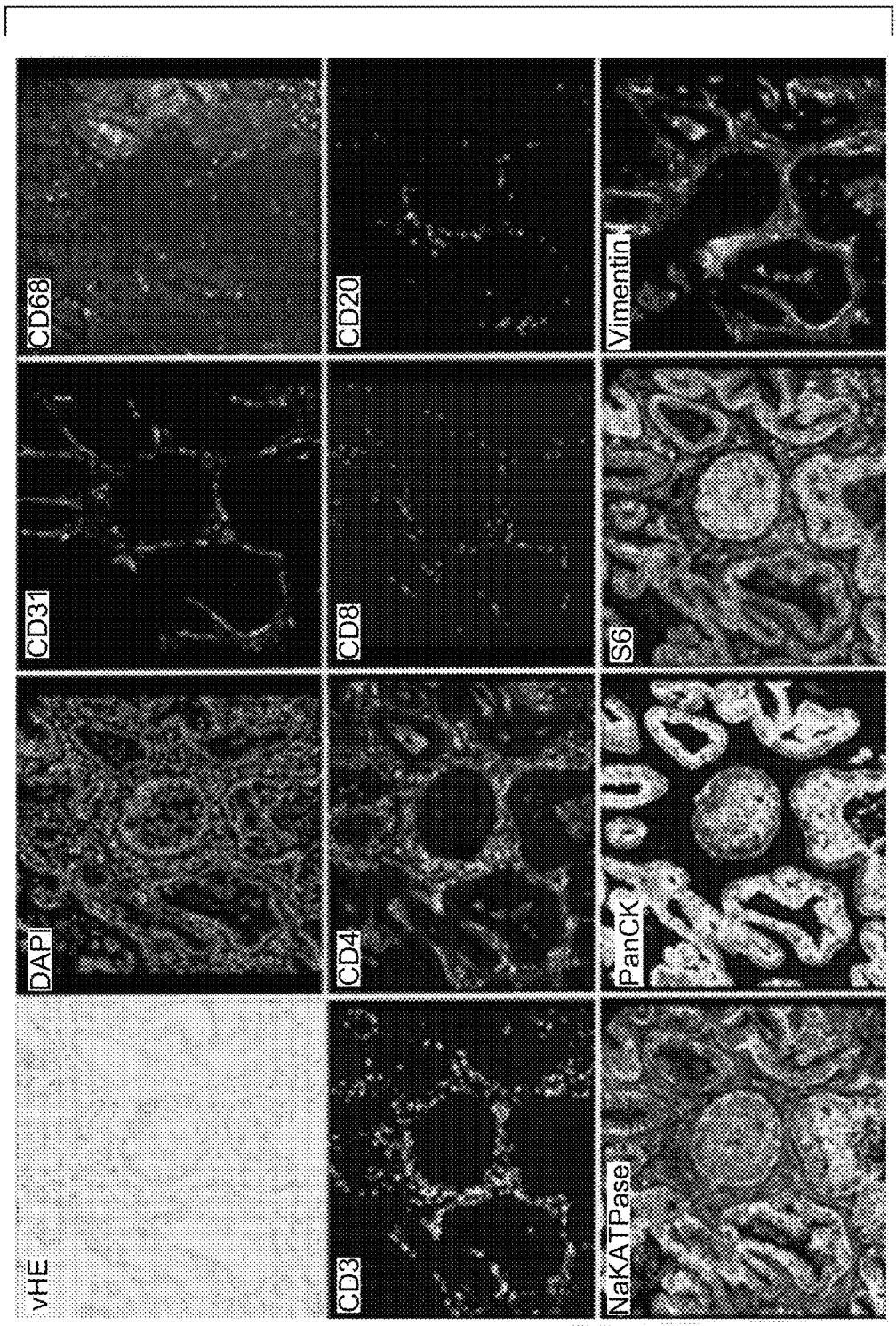
FIG. 6 is a panel of immune cell markers on a lung cancer case imaged on the same FOV.
Figure 7:
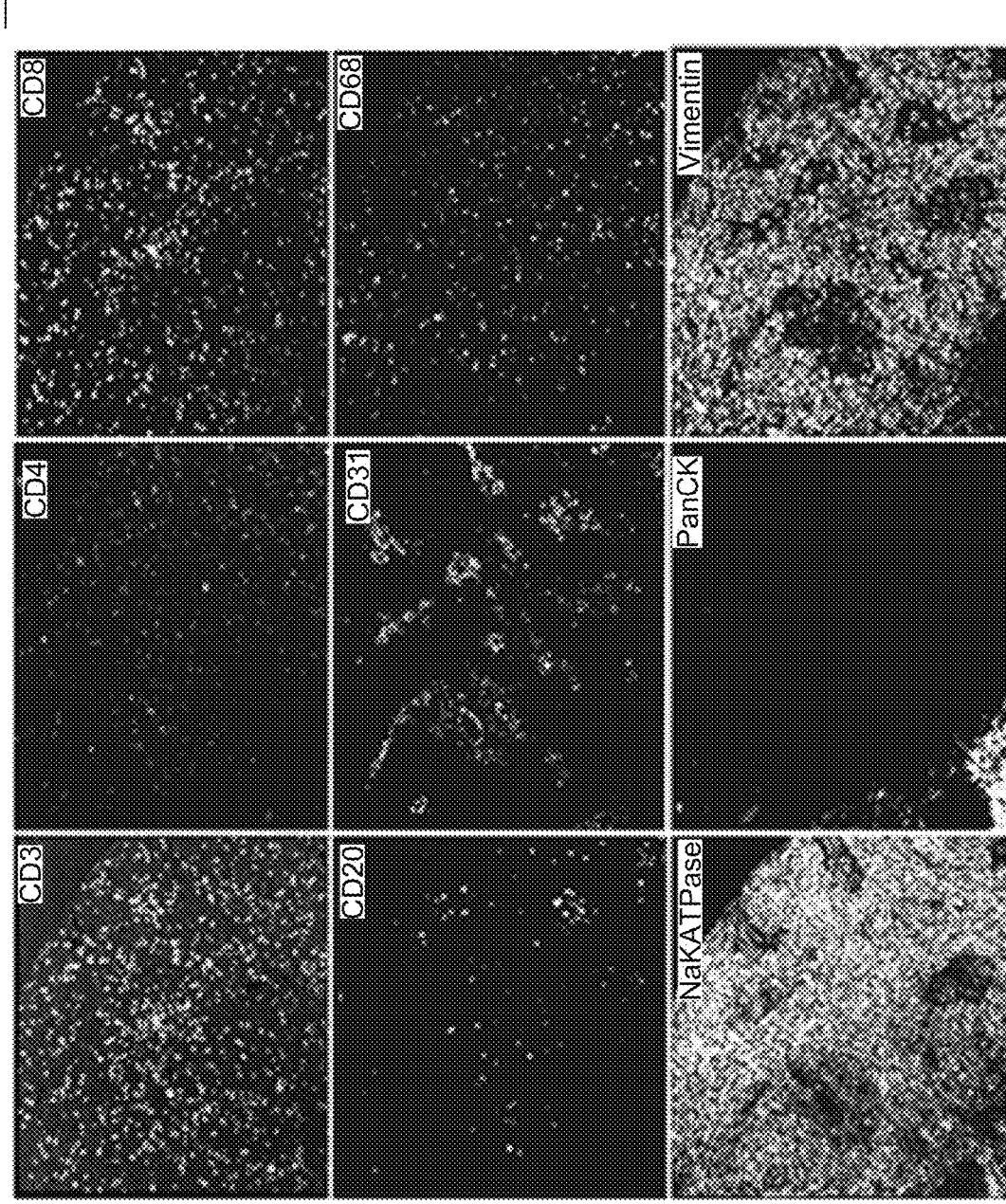
FIG. 7 is a panel of immune cell markers on a melanoma case imaged on the same FOV.
Figure 8:
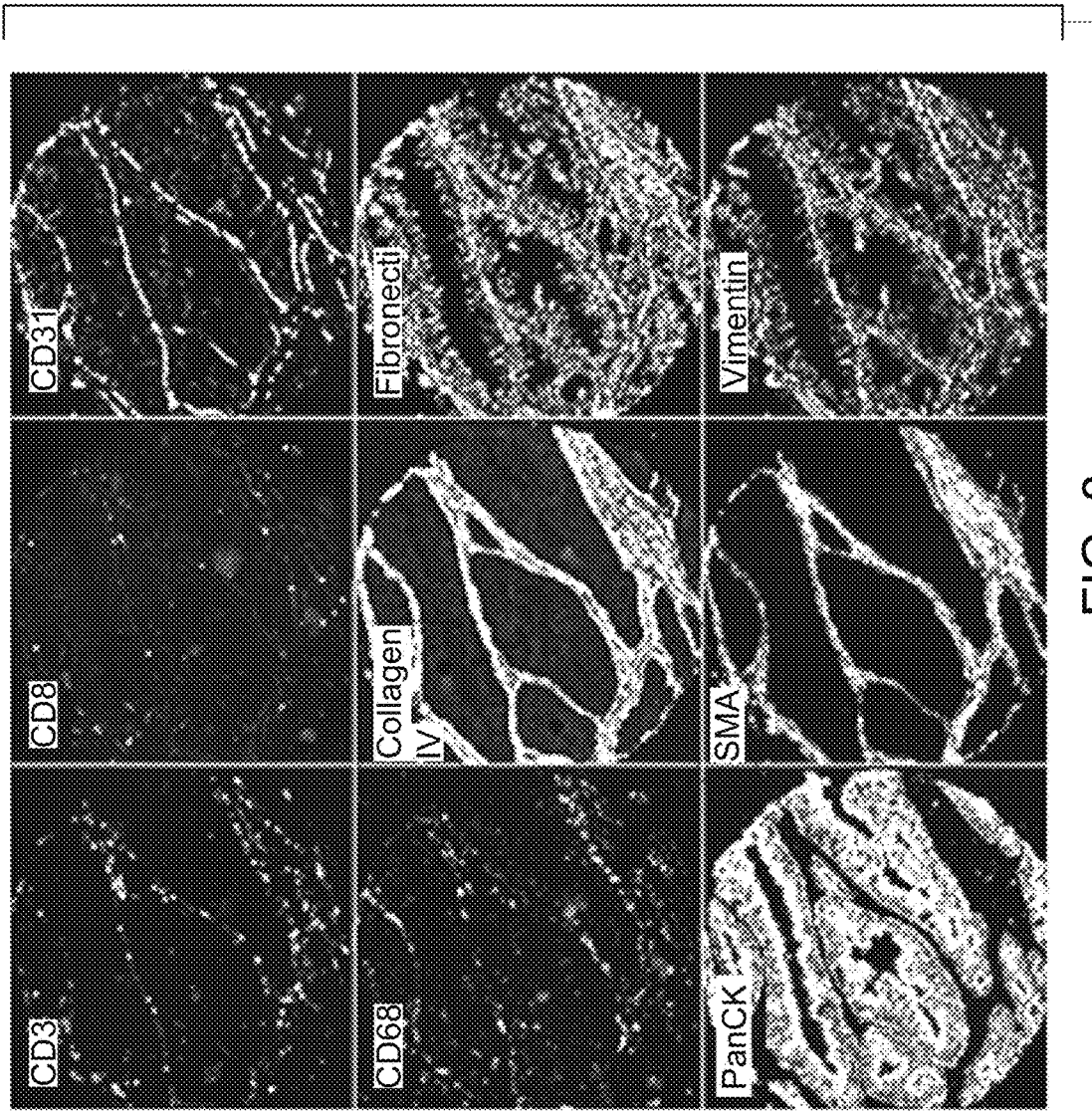
FIG. 8 is a panel of immune cell and segmentation markers for a tissue microarray core for a colorectal cancer case.

FIG. 6 represents five immune cell markers, (T cell, B cells and macrophage), one blood vessel marker, and four segmentation markers taken from a single case of lung cancer. FIG. 7 is a panel of five immune cell markers (T cell, B cells and macrophage), one blood vessel marker, and three segmentation markers taken from a single case of melanoma. FIG. 8 shows selected microenvironment features in a TMA core from a colorectal cancer.

Immune system predominantly exhibits two kinds of responses: innate and adaptive. Innate responses are represented by macrophages, neutrophils, basophils, eosinophils, dendritic cells (DCs), natural killer (NK) cells and NK T cells, whereas T cells like CD4+ T helper cells and CD8+ cytotoxic T cells exhibits adaptive immune response. Innate cells such as macrophages, mast cells and neutrophils can contribute to tumor angiogenesis. Tumor infiltration by such cells often correlates with a poor prognosis whereas infiltrating lymphocytes often correlates with a favorable prognosis.

Tristar 69571118 NSCLC prognosis tissue array with patient information was used for data analysis. Stromal segmentation QC check for each core was done and final cores were down selected. Five percent of the cores were discarded based on the following criteria (a) Low stromal area in the FOV (b) DAPI over segmentation due to tissue quality (c) FOV with weak DAPI stain. The following analyses were done with lung panel data: Prognostic clinicopathological variables as predictors of disease specific survival; Cancer subtype analysis of adenocarcinoma and squamous carcinoma cores; Survival analysis; Prognostic clinicopathological variables as predictors of disease specific survival.

In the lung study an univariate analysis of association between clinicopathological variables and patient survival (alive or non-tumoral death versus tumoral death) was performed by fitting a Cox-proportional hazard model and assessed the statistical significance by the likelihood-ratio test. Age and cancer stage were significantly associated with patient survival and therefore can be used as prognostic factors for patient survival. Age and cancer stage were adjusted for in the subsequent analyses to infer that the protein markers provided an improved model. Table 4 shows the clinical variables of a patient cohort in the lung TMA.

TABLE 4

Prognostic clinicopathologic variables as predictors of disease specific survival

| Clinical Variables | No of patients | Percentage | p-value |
|---|---|---|---|
| Pathological Diagnosis | | | 0.68 |
| Squamous | 55 | 38.50% | |
| Adenocarcinoma | 62 | 43.50% | |
| Bronchioloalveolar carcinoma | 6 | 4% | |
| Large cell, undifferentiated | 4 | 3% | |
| Adenosquamous | 3 | 2% | |
| Other mixed | 8 | 5.50% | |
| Other mixed | 5 | 3.50% | |
| Age | | | 0.009 |
| ≥65 | 83 | 58% | |
| <65 | 60 | 42% | |
| Sex | | | 0.518 |
| Female | 20 | 14% | |
| Male | 123 | 86% | |
| Race | | | NA |
| White | 143 | 100% | |
| Clinical Diagnosis | | | NA |
| Stage | | | |
| Ia, Ib, IIa, IIb combined | 127 | 89% | 0.0025 |
| III, IV combined | 16 | 11% | |
| Previous treatment | | | 0.011 |
| Neo adjuvant chemotherapy | 4 | 3% | |
| Neo adjuvant radiotherapy | 0 | | |
| No prior treatments | 139 | 97% | |
| Clinical response | | | 0.011 |
| No | 139 | 97% | |
| Partial | 4 | 3% | |
| Smoker | | | 0.541 |
| No | 16 | 11% | |

TABLE 4-continued

Prognostic clinicopathologic variables as predictors of disease specific survival

| Clinical Variables | No of patients | Percentage | p-value |
|---|---|---|---|
| Yes | 127 | 89% | NA |
| Census | | | |
| Alive or non-tumoral death | 93 | 65% | |
| Tumor death | 50 | 35% | |

In addition, 59 Adenocarcinoma versus 54 squamous carcinoma cores were compared to investigate whether two cancer subtypes may be separated using the immune marker positive cell fractions. Epithelium background was used to estimate the lower thresholds above which a stromal cell immune marker is identified as positive. The following threshold values were used for each marker:

| Marker | Threshold |
|---|---|
| CD3 | 297 |
| CD4 | 297 |
| CD8 | 126.5 |
| CD20 | 108 |
| CD68 | 695 |

Low threshold values were used to retain as many immune marker positive cells as possible. With the above liberal thresholds (high sensitivity): Observing multiple markers (3+, 5+) yielded statistically significant correlations.

Table 5 shows the area under the curve (AUC) for the additive model (0.54) and the interactions model (0.55) in the lower threshold condition. The analysis indicated that there is interaction effect among cells expressing multiple markers (CD3+ T cells, CD4+ Helper T cells, CD8+ Cytotoxic T cells, CD20+ B cells, CD 68 Macrophages). The additive model did not show statistically significant correlation.

TABLE 5

AUC for the additive model (0.65) and the interactions model (0.65) in the lower threshold condition

| Marker(s) | p-value | False Discovery Rate (%) | Model description |
|---|---|---|---|
| $CD3^+$ | 0.772 | 82 | Univariate logistic model |
| $CD4^+$ | 0.955 | 96 | Univariate logistic model |
| $CD8^+$ | 0.570 | 70 | Univariate logistic model |
| $CD20^+$ | 0.189 | 30 | Univariate logistic model |
| $CD68^+$ | 0.091 | 30 | Univariate logistic model |
| $CD3^+ \times CD4^+$ | 0.164 | 30 | Bivariate interaction |
| $CD4^+ + CD8^+$ | 0.756 | 82 | Bivariate additive |
| $CD4^+ \times CD8^+$ | 0.212 | 31 | Bivariate interaction |
| $CD4^+ \times CD68^+$ | 0.275 | 37 | Bivariate interaction |
| $CD4^+ \times CD20^+$ | 0.040 | 30 | Bivariate interaction |
| $CD3^+ \times CD4^+ \times CD8^+$ | 0.096 | 30 | trivariate interaction |
| $CD4^+ \times CD8^+ \times CD20^+$ | 0.162 | 30 | Trivariate interaction |
| $CD4^+ + CD8^+ + CD68^+$ | 0.156 | 30 | Trivariate additive |
| $CD4^+ \times CD8^+ \times CD68^+$ | 0.110 | 30 | Trivariate interaction |
| $CD3^+ + CD4^+ + CD8^+ + CD20^+ + CD68^+$ | 0.168 | 30 | Multivariate additive |
| $CD3^+ \times CD4^+ \times CD8^+ \times CD20^+ \times CD68^+$ | <0.001 | 1 | Multivariate interactions |

Table 6 shows the area under the curve (AUC) for the additive model (0.65) and the interactions model (0.65) in the higher threshold condition. The analysis indicated that there is interaction effect among cells expressing multiple markers (CD3, CD4, CD8, CD20, CD68). The additive model did not show statistically significant correlation.

TABLE 6

AUC for the additive model (0.65) and the interactions model (0.65) in the higher threshold condition

| Marker(s) | p-value | False Discovery Rate (%) | Model description |
|---|---|---|---|
| $CD3^+$ | 0.610 | 61 | Univariate logistic model |
| $CD4^+$ | 0.268 | 33 | Univariate logistic model |
| $CD8^+$ | 0.189 | 28 | Univariate logistic model |
| $CD20^+$ | 0.437 | 47 | Univariate logistic model |
| $CD68^+$ | 0.068 | 11 | Univariate logistic model |
| $CD4^+ + CD8^+$ | 0.006 | 2 | Bivariate additive |
| $CD3^+ \times CD4^+$ | 0.051 | 9 | Bivariate interaction |
| $CD4^+ \times CD8^+$ | 0.003 | 1 | Bivariate interaction |
| $CD4^+ \times CD68^+$ | 0.290 | 33 | Bivariate interaction |
| $CD4^+ \times CD20^+$ | 0.274 | 33 | Bivariate interaction |
| $CD3^+ \times CD4^+ \times CD8^+$ | 0.009 | 2 | Trivariate interaction |
| $CD4^+ \times CD8^+ \times CD20^+$ | 0.003 | 1 | Trivariate interaction |
| $CD4^+ + CD8^+ + CD68^+$ | 0.003 | 1 | Trivariate additive |
| $CD4^+ \times CD8^+ \times CD68^+$ | <0.0001 | 0 | Trivariate interaction |
| $CD3^+ + CD4^+ + CD8^+ + CD20^+ + CD68^+$ | 0.007 | 2 | Multivariate additive |
| $CD3^+ \times CD4^+ \times CD8^+ \times CD20^+ \times CD68^+$ | <0.0001 | 0 | Multivariate interactions |

Table 7 shows survival analysis with "low thresholds" based on the epithelium background. In addition to the immune marker positive fractions, the mean and the standard deviation for the immune markers within the stromal area were computed. Based on a univariate screening of data from moments and hotspots, cells positive for CD3 or CD8 marker were found to be most strongly associated with patient survival.

TABLE 7

P-value of association of Immune marker with patient survival

| Marker | p-value: Immune marker positive fractions (hotspot) | p-value: Mean Immune marker (moments) | p-value: Std. Dev. Immune marker (moments) |
|---|---|---|---|
| CD3 | 0.026 | 0.743 | 0.511 |
| CD4 | 0.058 | 0.399 | 0.163 |
| CD8 | 0.301 | 0.007 | 0.383 |

TABLE 7-continued

P-value of association of Immune marker with patient survival

| Marker | p-value: Immune marker positive fractions (hotspot) | p-value: Mean Immune marker (moments) | p-value: Std. Dev. Immune marker (moments) |
|---|---|---|---|
| CD20 | 0.081 | 0.032 | 0.266 |
| CD68 | 0.060 | 0.147 | 0.152 |
| CD163 | 0.678 | 0.129 | 0.866 |

Figure 9:
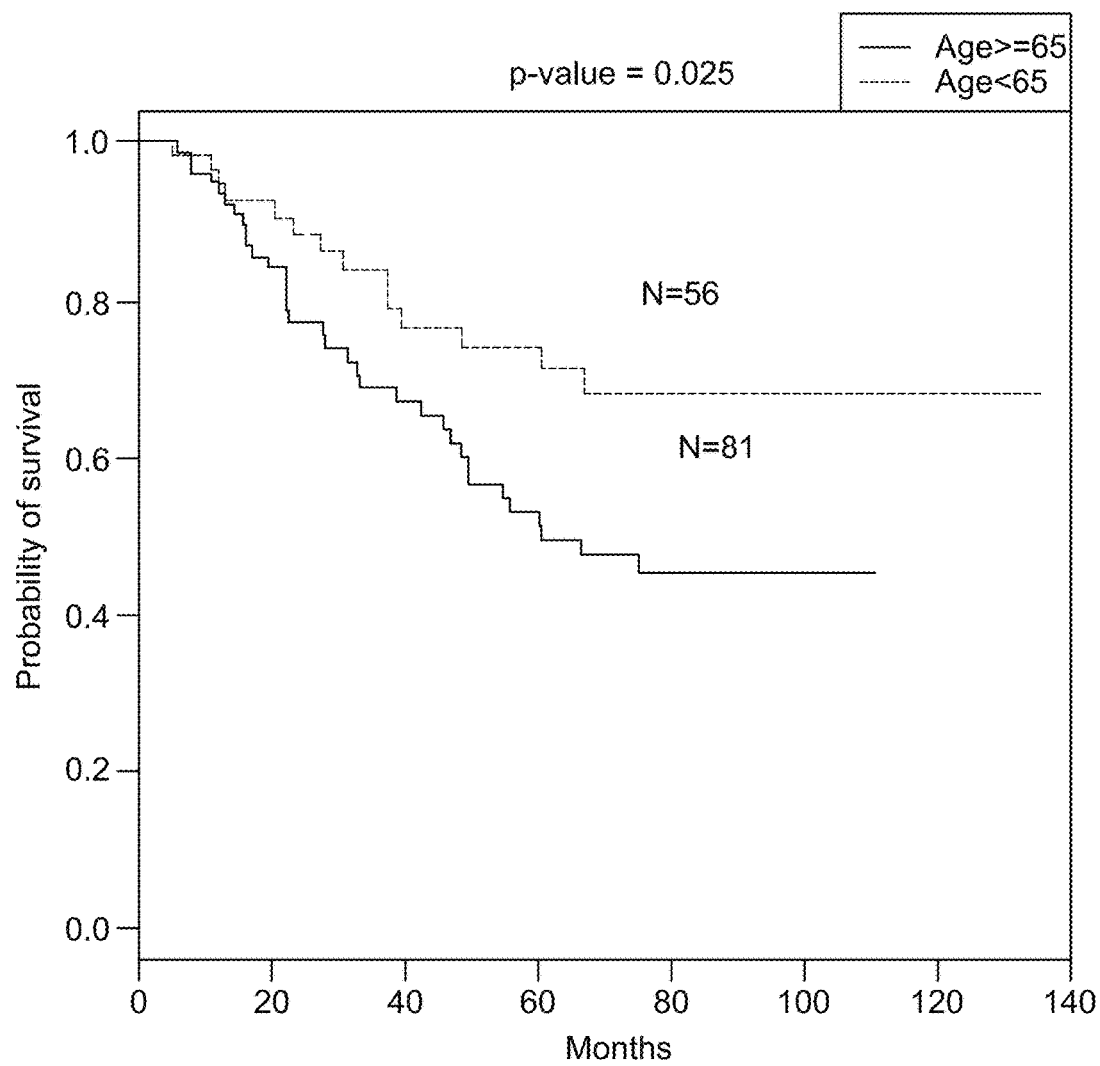
FIG. 9 is a plot of survival rates by age for a lung cancer cohort.
Figure 10:
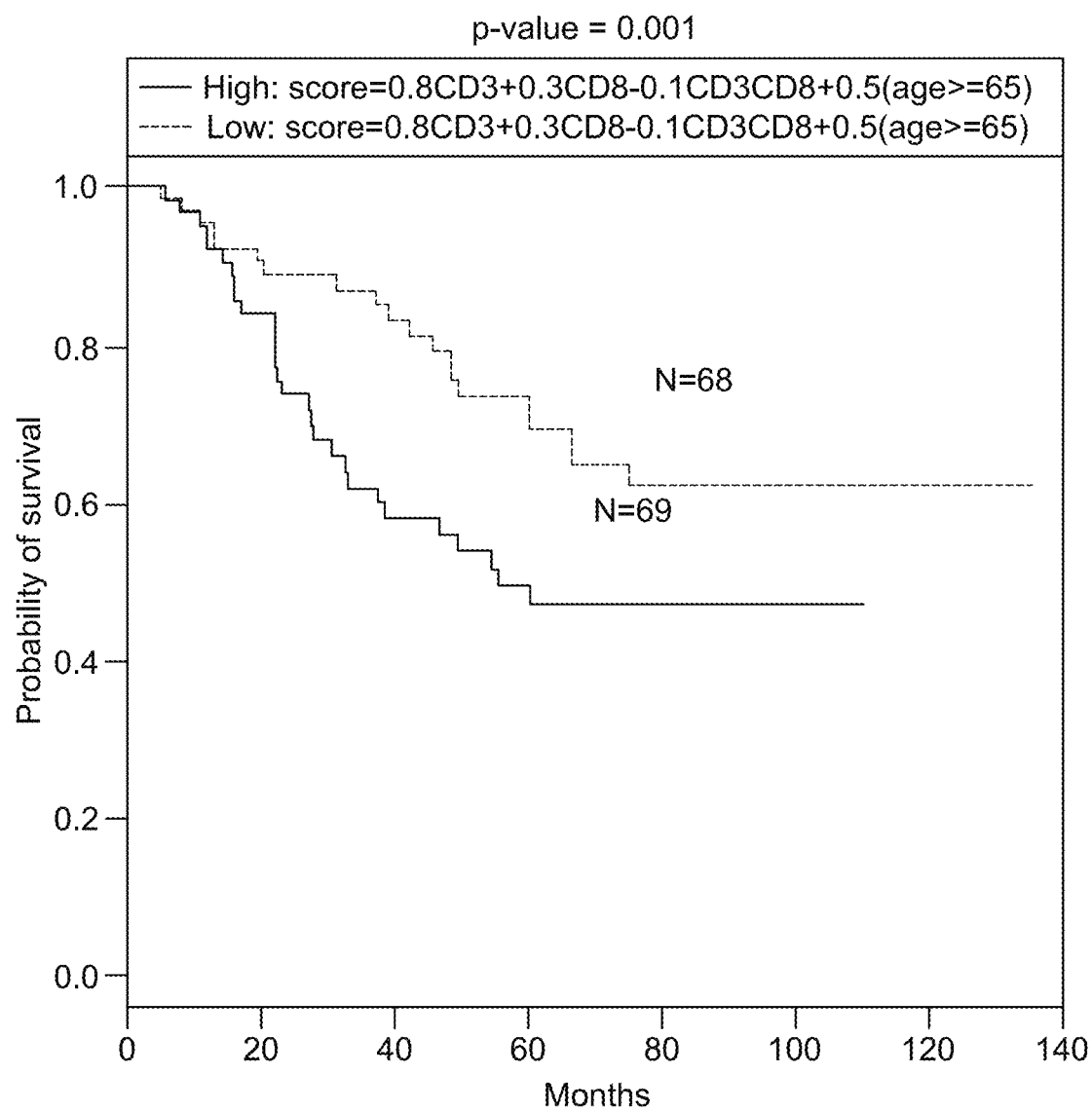
FIG. 10 is a model of survival rates using a quantitative in situ biological sample characterization of cytotoxic T-lymphocytes in total leukocyte population (CD3 and CD8) of a lung cancer cohort according to an embodiment of the present disclosure.
Figure 11A:
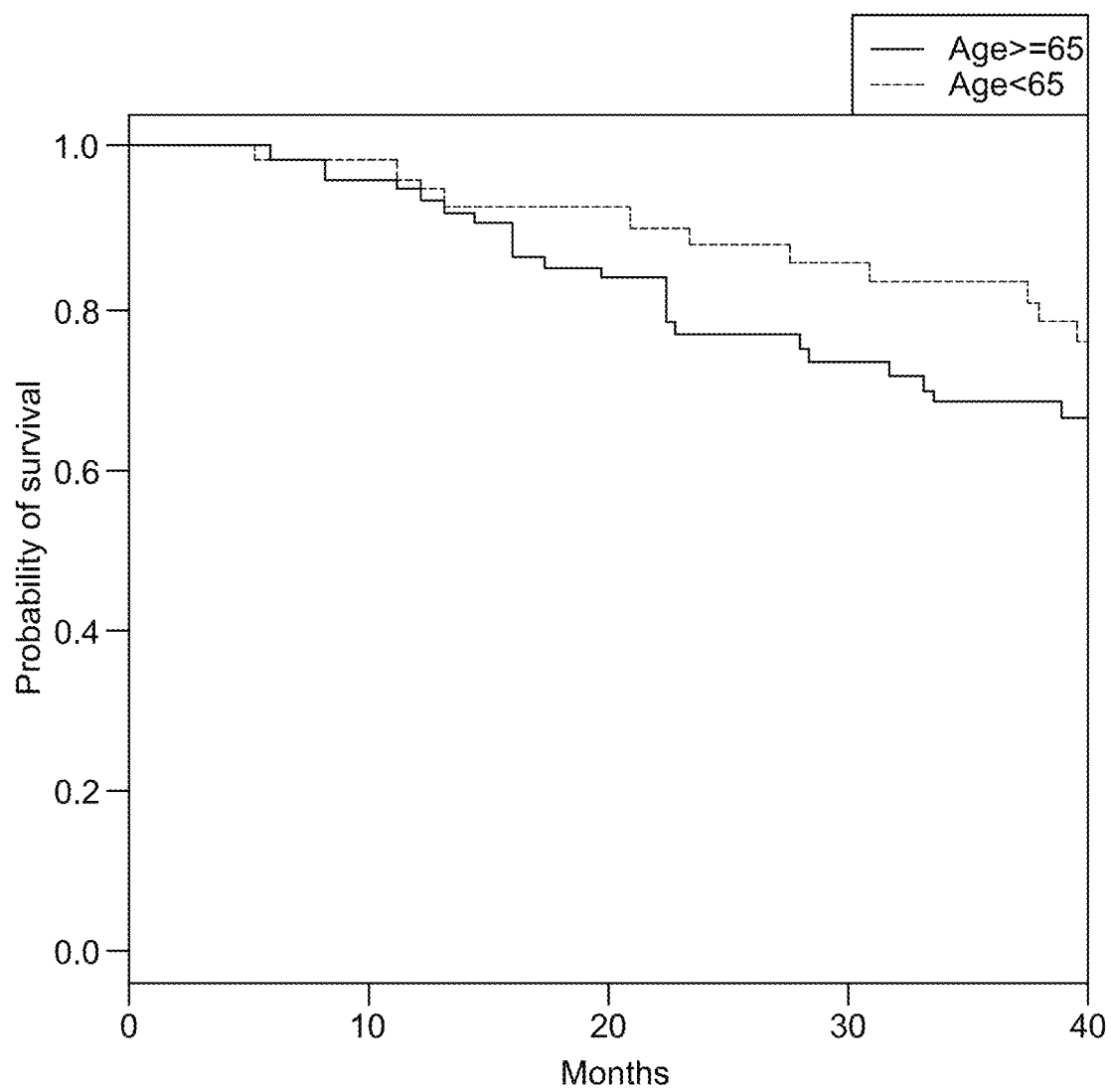
FIG. 11A is a plot of survival rates by age.
Figure 11B:
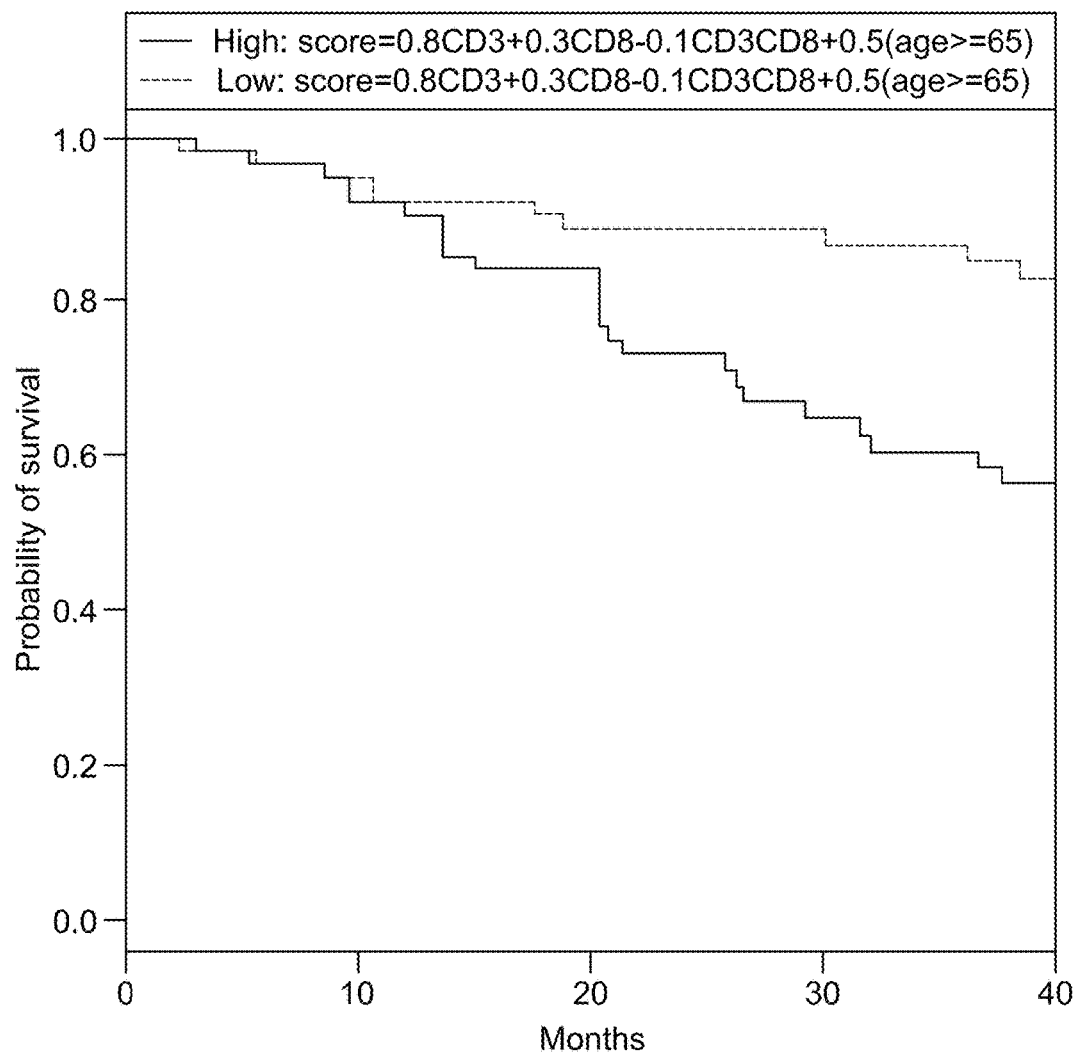
FIG. 11B represents survival rates using a quantitative in situ biological sample characterization of cytotoxic T-lymphocytes and patient age in a lung cancer cohort according to an embodiment of the present disclosure.
Figure 12A:
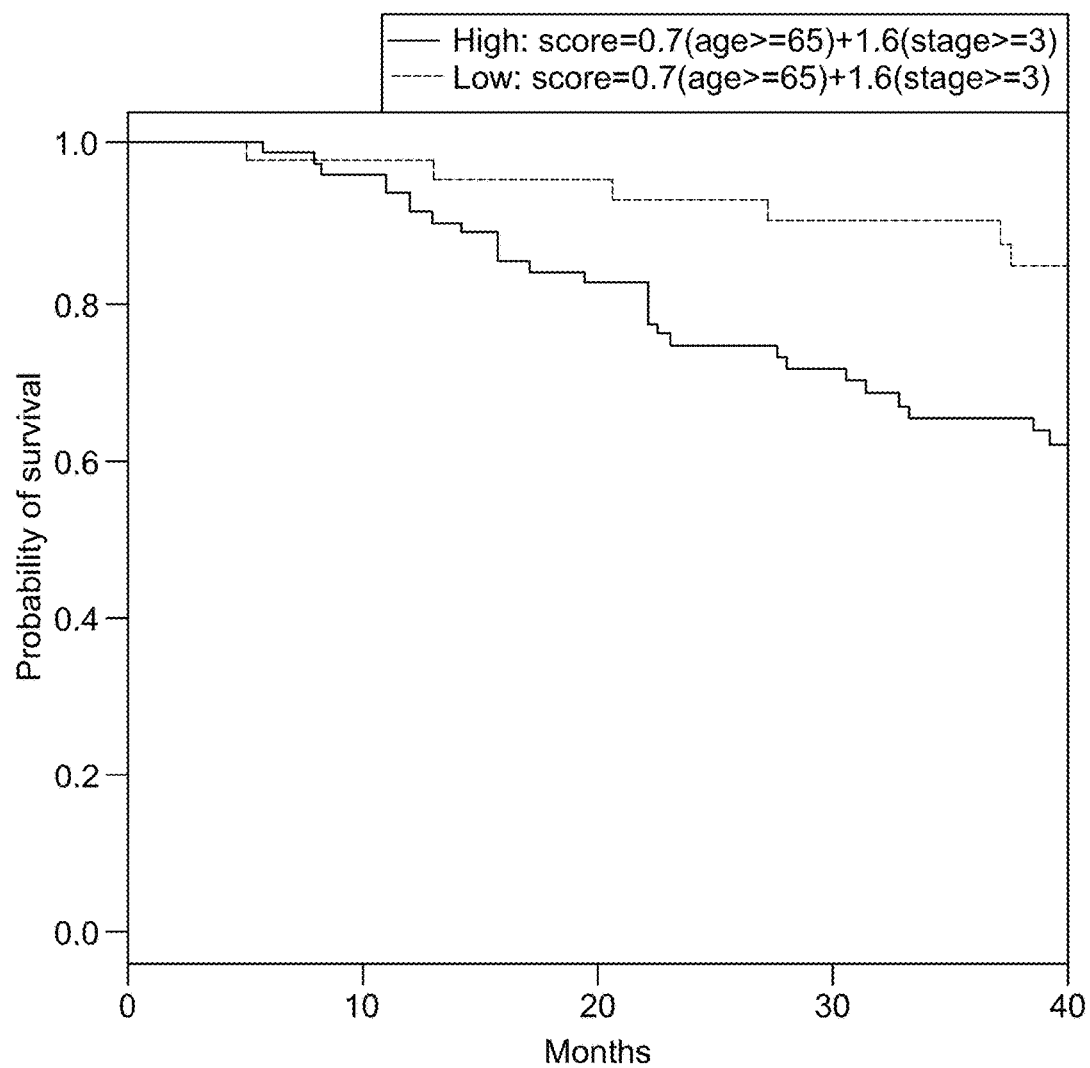
FIG. 12A is a plot of survival rates by age and stage.
Figure 12B:
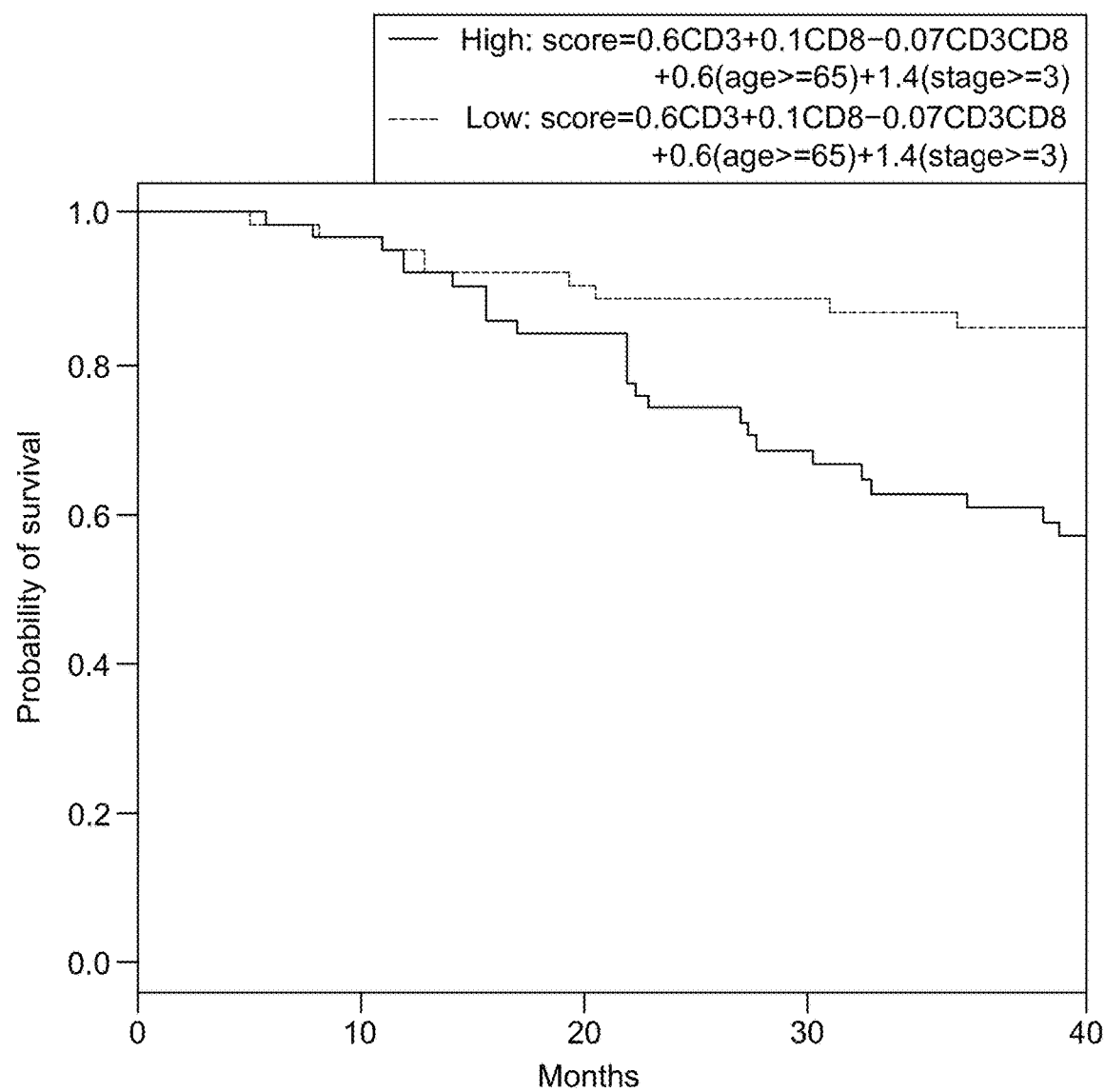
FIG. 12B represents survival rates using a quantitative in situ biological sample characterization of cytotoxic T-lymphocytes, patient age and stage in a lung cancer cohort according to an embodiment of the present disclosure.

The model incorporating CD3 and CD8 markers appears to be better at predicting patient survival than the model using the age alone, especially during the first 40 months post cancer treatment. FIG. 9 is a graph of survival using age and FIG. 10 is a graph of survival using age and CD3 and CD8 markers of first 140 months assessed using the disclosed techniques. FIGS. 11 and 11b represents survival rates using cytotoxic T-lymphocytes and patient age for first 40 months, whereas FIGS. 12a and 12b represents survival rates using cytotoxic T-lymphocytes, patient age and stage for first 40 months, in the lung cancer cohort.

To analyze the association between immune cell infiltration and colorectal cancer (CRC) prognosis, populations of various immune cells relative to all cells in the whole TMA core, in the epithelial regions, and the stromal regions were examined. After multiplexed immunofluorescence, image segmentation, and quality control, distributions of cell-level staining for each marker were visualized as box-plots and histograms of each the three TMAs. Visual inspection indicated that slide level normalization was required to analyze the whole cohort. Two normalization methods were used: median centering and quartile normalization (25th, 50th and 75th quantiles were aligned). Immune cell types included CD3+ T-lymphocytes, CD8+ T-lymphocytes, CD3+/CD8− T-lymphocytes (equivalent to CD4+ T-lymphocytes), Claduin1+ neutrophils, CD68+ macrophages, CD20+ B-lymphocytes and CD79+ B-lymphocytes. CD31+ cells (endothelial cells and unspecified immune cells), and epithelial cell markers pancytokeratin and E-cadherin were also assessed. Two methods were used to define positive cells: supervised marker annotations were performed and quantitative features extracted were used to derive cell level positivity thresholds; and unsupervised analysis (moments and hotspots) included the proportion of cells above the 50th and 95th quantiles, cell-level marker standard deviation, and cell-level coefficient of variation. Cells were localized to either the epithelial or stromal region based on their position relative to the epithelial mask. Prognostic association of each cell feature (including location) with patient survival was assessed using univariate Cox proportional hazards modeling. Features exhibiting a predicted false discovery rate (FDR) of <0.10 were cross validated using receiver operator characteristic (ROC). Markers with ROC>0.6 were selected for further analysis including stage specific prognosis. Kaplan Meier survival analysis was analyzed using the log-rank test to evaluate the significance of prognostic findings.

Standard clinical features were analyzed with respect to prognosis. Stage and grade were found to have significant associations with outcome, consistent with current clinical management of CRC. Counter to currently accepted prognostic clinical features, number of lymph nodes examined was not significantly related to outcome. Features with significant associations with outcome were visualized in Kaplan-Meier survival plots. Grade appears to be mostly associated with tumor stage, as the survival curves are better separated in the whole cohort analysis (Table 8).

Unsupervised analysis—two normalization techniques yield similar results: high level tumor infiltration by claudin1+ neutrophils, CD3+ T-lymphocytes and CD8+ T-lymphocytes are markers of favorable prognosis in localized colorectal cancer (Table 9 and 10) as described above (moments and hotspots analysis). Supervised analysis—high level tumor infiltration of CD68+ macrophages, CD3+, CD4+(defined by CD3+/CD8− staining) and CD8+ T-lymphocytes are markers of favorable prognosis in localized colorectal cancer (Table 11). In both cases, prognostic features occur in stromal and/or epithelial specific localization of the cell of interest. All features are strong predictors in the whole cohort (stages I-III), and weaken in stage specific analysis.

In the unsupervised analysis of immune cell features using quartile normalization, seven features of immune cells in colorectal cancer representing CD3+T-lymphocytes, CD8+ T-lymphocytes, and claudin1+ neutrophils were significantly associated with prognosis as defined above. In unsupervised analysis using median centering, 17 features representing five markers were significantly associated with disease prognosis. Cell types showing prognostic value included CD8+ T-lymphocytes, CD3+ T-lymphocytes, CD31+ cells, and claudin1+ neutrophils (Table 10). Results from each normalization approach yielded significant features with tumor stroma and epithelium specific localization patterns.

In the supervised analysis, eight features representing four immune cell types were associated with outcomes in the whole cohort. Features with significant associations with a favorable prognosis included CD3+ T-lymphocytes in the tumor stroma, CD4+ T-lymphocytes in the tumor stroma, CD68+ cells in the tumor stroma and CD8+ T-lymphocytes in the tumor stroma and CD8+ T-lymphocytes in the epithelium, demonstrating localization specific immune cell prognostic features.

Table 8: summary of clinical variables and relationship with recurrence time: Summary of standard clinical features of the colorectal cancer cohorts. P-value indicates association with disease recurrence in univariate Cox proportional Hazards model.

TABLE 8

Summary of clinical variables and relationship with recurrence time

| Clinical variables | | N or average | Percent or sd | p-value |
|---|---|---|---|---|
| Age | | 65 | 12 | 0.3 |
| Gender | | 361 | 49% | 0.79 |
| Grade | 1 | 116 | 16% | 0.0005 |
| | 2 | 530 | 71% | |
| | 3 | 85 | 11% | |
| PT | 1 | 79 | 11% | <0.0001 |
| | 2 | 162 | 22% | |
| | 3 | 445 | 60% | |
| | 4 | 56 | 8% | |
| PN | 0 | 487 | 65% | <0.0001 |
| | 1 | 161 | 22% | |
| | 2 | 93 | 12% | |
| Stage | 1 | 198 | 27% | <0.00001 |
| | 2 | 277 | 38% | |
| | 3 | 252 | 35% | |
| ND.POS | | 3 | 12 | 0.11 |
| ND.XAM | | 14 | 9.8 | 0.34 |
| Recurrence days | | 640 | Range (0, 3458) | NA |
| Follow up days | | 1503 | Range (0, 4742) | NA |

Table 9 shows unsupervised quartile normalized prognostic features. Seven features representing three immune cell types were associated with colorectal cancer recurrence as defined by meeting false discovery rate and ROC criteria (feature Q<0.10 and feature ROC AUC >0.6).

| Feature | Tissue localization | Natural log (hazard ratio) | p-value | False Discovery Rate |
|---|---|---|---|---|
| CD8 standard deviation | epithelium | −2.375 | <0.000001 | <0.00001 |
| CD8 standard deviation | Total tissue | −2.038 | <0.000001 | <0.00001 |
| CD3 standard deviation | stroma | −1.277 | <0.000001 | <0.00001 |
| CD8 standard deviation | Stroma | −1.600 | <0.000001 | <0.00001 |
| Claudin 1 standard deviation | stroma | −0.797 | 0.000027 | 0.00049 |
| CD3 standard deviation | Total tissue | −1.173 | 0.000086 | 0.00117 |
| CD8 95 percentile | epithelium | −0.043 | 0.027390 | 0.09542 |

Table 10 shows significant prognostic features from median centered unsupervised data analysis. Eighteen features representing 5 cell types including Claudin1+ neutrophils, CD3+ T-lymphocytes and CD8+ T-lymphocytes were significantly associated with disease recurrence in Cox proportional hazards modeling.

| Feature | Tissue localization | Natural log (hazard ratio) | p-value | False Discovery Rate |
|---|---|---|---|---|
| CD3 mean | stroma | −0.472 | 2.03E−05 | 0.000129 |
| CD3 mean | Total tissue | −0.537 | 2.84E−05 | 0.000164 |
| CD31 CV | epithelium | 4.558 | 0.001108 | 0.004433 |
| CD8 CV | epithelium | 0.168 | 4.15E−08 | 3.20E−07 |
| CD8 CV | stroma | 0.286 | 3.32E−11 | 8.95E−10 |
| CD8 CV | Total tissue | 0.286 | 1.36E−10 | 2.93E−09 |
| CD8 mean | epithelium | −0.598 | 1.57E−09 | 1.99E−08 |
| CD8 mean | stroma | −0.543 | 2.06E−08 | 1.85E−07 |
| CD8 mean | Total tissue | −0.598 | 2.97E−09 | 3.21E−08 |
| Claudin 1 CV | stroma | 0.920 | 7.88E−15 | 8.51E−13 |
| Claudin 1 CV | Total tissue | 1.131 | 1.13E−12 | 6.13E−11 |
| Claudin 1 mean | epithelium | −0.468 | 1.66E−09 | 1.99E−08 |
| Claudin 1 mean | stroma | −0.329 | 1.30E−09 | 1.99E−08 |
| Claudin 1 mean | Total tissue | −0.381 | 5.64E−09 | 5.54E−08 |
| Claudin 1 standard deviation | epithelium | 1.298 | 2.00E−11 | 7.20E−10 |
| Claudin 1 standard deviation | stroma | 0.530 | 2.89E−05 | 0.000164 |
| Claudin 1 standard deviation | Total tissue | 0.728 | 9.35E−08 | 6.73E−07 |

Table 11 shows supervised annotation based features with associations with prognosis. Image annotations of positive regions of interest were used to define thresholds for positivity of CD68, CD3, CD8, CD20, CD79 and ALDH1. The proportion of cells positive for each marker was computed in the entire field of view, the stromal region, and the epithelial region for each case. This proportion was then used as a feature in univariate Cox proportional hazards models to predict the likelihood of disease recurrence. Eight features representing four cell types were found to be predictive of disease recurrence (CD68=macrophages; CD3=total T-lymphocytes; CD4T=CD4+ T-lymphocytes (defined as CD3+/CD8−); and CD8=CD8+ T-lymphocytes).

TABLE 11

Describes supervised annotation based features with associations with prognosis

| Feature | Tissue localization | Natural log (hazard ratio) | p-value | False Discovery Rate |
|---|---|---|---|---|
| CD68 | stroma | −1.860 | 7.82E−07 | 3.05E−05 |
| CD3 | stroma | −3.722 | 5.83E−06 | 0.000104 |
| CD4T | stroma | −4.401 | 9.44E−06 | 0.000104 |
| CD68+/ALDH1+ | stroma | −2.062 | 1.06E−05 | 0.000104 |
| CD68 | Total tissue | −1.658 | 0.000125 | 0.000977 |
| CD8_str | Stroma | −8.794 | 0.001012 | 0.005636 |
| CD8_tot | Total tissue | −12.526 | 0.001771 | 0.008632 |
| CD68_ALDH1_tot | Total tissue | −1.731 | 0.002045 | 0.00886 |

Figure 13:
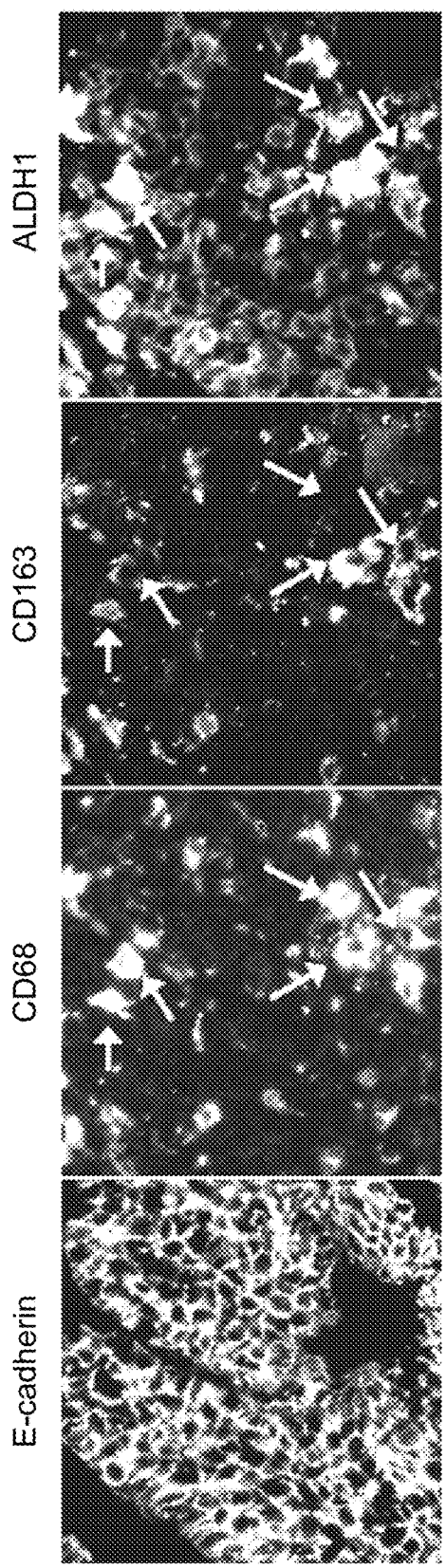
FIG. 13 shows differential expression of CD68, CD163 and ALDH1 in the same macrophage cells in colon cancer tissue.

In addition to analysis of standard immune cell subtypes we calculate the % of dual and single positive cells based on supervised and unsupervised method in both colorectal cancer and lung cancer Supervised annotation: The derived threshold in colorectal cancer is applied to the single cell data, and each cell is scored to be either positive or negative. Next, the percentage of positive cells is calculated in the epithelium or stromal regions. For markers co-expressed in the same cell, we declare double positive cells if both markers are positive in a given cell. Finally, the proportion of positive cells in the epithelium or stromal regions is calculated. In one example, co-expression of 2 markers, one being an immune cell marker (CD68/CD163), and the other being a functional marker (ALDH1) was examined (FIG. 13). The relative % of these cells is listed in Table 12.

TABLE 12

Shows the percentage of single and dual positive cells for selected markers.

| Immune cell subsets | Tissue localization | % cells |
|---|---|---|
| ALDH1+ | epithelium | 55% |
| ALDH1+ | Stroma | 65% |
| CD163+ | Epithelium | 13% |
| CD163+ | Stroma | 21% |
| CD68+ | Epithelium | 18% |
| CD68+ | Stroma | 31% |
| CD163+/ALDH1+ | Epithelium | 8% |
| CD163+/ALDH1+ | Stroma | 16% |
| CD68+/ALDH1+ | Epithelium | 11% |
| CD68+/ALDH1+ | Stroma | 24% |

Unsupervised annotation: In lung panel, for each patient, protein marker specific threshold was used to determine whether a given cell was positive for given protein marker. The cell count was pooled for 137 patients in the TMA and the fraction of total stromal cells positive for the given protein marker was calculated. Similarly, for each patient, the number of multiple marker coexpressing cells was calculated. The counts were pooled across all 137 patients to calculate the fraction of total stromal cells co-expressing multiple protein markers (Table 13).

| Immune cell subsets | % stromal cells |
|---|---|
| $CD3^+$ | 38 |
| $CD4^+$ | 46 |
| $CD8^+$ | 19 |
| $CD20^+$ | 7 |
| $CD68^+$ | 30 |

-continued

| Immune cell subsets | % stromal cells |
| --- | --- |
| CD3$^+$CD4$^+$ | 29 |
| CD3$^+$CD8$^+$ | 17 |
| CD4$^+$CD8$^+$ | 14 |
| CD3$^+$CD4$^+$CD8$^+$ | 13 |
| CD3$^+$CD4$^+$CD8$^+$CD20$^+$ | insignificant |
| CD3$^+$CD4$^+$CD8$^+$CD68$^+$ | insignificant |

Table 13 shows percentage of stromal cell showing dual and single positive marker expression in the lung cohort. CD3$^+$, CD4$^+$, CD8$^+$ represents T cells; CD20$^+$ represents B cells and CD68$^+$ represents macrophage. CD3$^+$+CD4$^+$, CD3$^+$+CD8$^+$ and CD4$^+$+CD8$^+$ represents T cells expressing dual markers whereas CD3$^+$CD4$^+$CD8$^+$ represents T cells expressing all three markers.

The disclosed experimental results show that immune cell marker localization and types within a tumor sample may be used to identify and/or provide prognoses for cancer cases. While cells were localized to either the epithelial or stromal region based on their position relative to the epithelial mask and as such used to identify epithelial cancers, the same methodology and techniques are applicable to the analysis of non-epithelial cancers as well based on relative position and biomarkers identified.

Probes and Binders

Provided herein are imaging techniques that may be used in conjunction with appropriate imaging molecules, such as probes and binders. A probe may include an agent including a binder and a signal generator. In some embodiments, the binder and the signal generator of the probe are embodied in a single entity (e.g., a radioactive or fluorescent molecule capable of binding a target). In alternative embodiments, the binder and the signal generator are embodied in discrete entities (e.g., a primary antibody capable of binding target and labeled secondary antibody capable of binding the primary antibody). In particular embodiments, the probes may include probes for multiple immune markers or targets as well as probes for morphological features of cells, segmentation markers, etc.

In certain embodiments, the probes may include probes that delineate immune cell subtypes. This include but not limited to one or more of the following markers: CD1a, CD3, CD4, CD7, CD8, CD8a, CD11c, CD11b, CD14, CD16 CD19, CD20, CD22, CD23, CD25, CD27, CD28, CD31, CD30, CD32, CD33, CD34, CD35, CD38, CD40, CD40L CD45, CD45RO, CD45RA, CD47, CD57, CD39, CD100, CD 68, CD70, ALDH1, CD83, CD80, CD86 CD163, CD206 FoxP3, claudin1, CD79, MMP7, MMP9, MMP2, MMP8, arginase, IL2, IL4, IL8, IL10, IL12, IL17a, IL18, TNF alpha, TGF-beta, IFNG, CCR-7, CXCL 8, CXCL9, CXCL10, CXCL11, CXCL13, CCL2, CCL5, CCL17, CCL22, IL12p40, MHCI, MHC II, CD56, TSLP GZM-B, GNLY, REN, IRF1 ITGAE, LAG 3, Tie2, PD1, PD11, CCLA4, TIM3, VISTA, B7H3, B7H4, FasL, HLADR, NKT, B7RP1, ICOS, HVEM, CD137, CD137L, Ox40, Ox40L, GALS, KIR. In addition, the probes may include probes for stromal markers such as vimentin, SMA, S100, collagen IV, and fibronectin and probes for segmentation markers (e.g., DAPI) for segmentation analysis. It should be understood that the disclosed probes-markers are provided as examples, and any suitable probe and/or marker may be used in conjunction with the disclosed techniques. Further, it should be understood that the probes may include a combination of markers such as immune cells markers, morphological features, and segmentation markers.

A binder may be a biological molecule that may non-covalently bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection. For example, a target in the sample may include a ligand and the binder may include a receptor or a target may include a receptor and the probe may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

A signal generator may be a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators useful in the inventive methods include, for example, a chromophore, a fluorophore, a Raman-active tag, a radioactive label, an enzyme, an enzyme substrate, or combinations thereof. As stated above, with regard to the probe, the signal generator and the binder may be present in a single entity (e.g., a target binding protein with a fluorescent label or radiolabel). And, in other embodiments the binder and the signal generator are discrete entities (e.g., target receptor protein and antibody against that particular receptor protein) that associate with each other prior to or upon introduction to the sample. A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared, and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

In particular embodiments, the signal generators may be fluorophores, or chemical compounds, which when excited by exposure to a particular wavelength of light, emit light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron™ Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

Binding, specific binding, or specificity of a probe for a marker occurs when molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions (i.e., a pH of about 6 to about 8 and temperature ranging from about 0° C. to about 37° C.).

In some embodiments, the present methods may employ probes that do not include an intrinsic signal generator. In some alternative embodiments, the probe does include a binder capable of binding to the target and a signal generator capable of providing a detectable signal. Thus, in some embodiments, the binder and the signal generator are not be associated to each other and may be present as a mixture or as separate components that associate following sequential application of the binder and signal generator to the biological sample. In alternate embodiments, the binder and the signal generator may be associated to each other. As used herein, "associated" generally refers to two entities (for example, binder and signal generator) stably bound to one another by any physicochemical means. The nature of the association may be such that it does not substantially impair the effectiveness of either entity. A binder and a signal generator may be associated to each other through covalent or non-covalent interactions. Non-covalent interactions may include, but are not limited to, hydrophobic interactions, ionic interactions, hydrogen-bond interactions, high affinity interactions (such as, biotin-avidin or biotin-streptavidin complexation), or other affinity interactions.

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, PNA sequences, and peptide nucleic acid sequences); Protein A/antibody; Protein G/antibody; nucleic acid/nucleic acid binding protein; or polynucleotide/polynucleotide binding protein.

For example, in some embodiments, a binder may be sequence-specific. A sequence-specific binder may include a nucleic acid and the binder may be capable of recognizing a particular linear arrangement of nucleotides or derivatives thereof in the target. In some embodiments, the linear arrangement may include contiguous nucleotides or derivatives thereof that may each bind to a corresponding complementary nucleotide in the binder. In an alternate embodiment, the sequence may not be contiguous as there may be one, two, or more nucleotides that may not have corresponding complementary residues on the probe. Suitable examples of nucleic acid-based binders may include, but are not limited to, DNA or RNA oligonucleotides or polynucleotides. In some embodiments, suitable nucleic acids may include nucleic acid analogs, such as dioxygenin dCTP, biotin dcTP 7-azaguanosine, azidothymidine, inosine, or uridine.

In certain embodiments, both the binder and the target may include nucleic acids. In some embodiments, a nucleic-acid based binder may form a Watson-Crick bond with the nucleic acid target. In another embodiment, the nucleic acid binder may form a Hoogsteen bond with the nucleic acid target, thereby forming a triplex. A nucleic acid binder that binds by Hoogsteen binding may enter the major groove of a nucleic acid target and hybridizes with the bases located there. Suitable examples of the above binders may include molecules that recognize and bind to the minor and major grooves of nucleic acids (for example, some forms of antibiotics). In certain embodiments, the nucleic acid binders may form both Watson-Crick and Hoogsteen bonds with the nucleic acid target (for example, bis PNA probes are capable of both Watson-Crick and Hoogsteen binding to a nucleic acid).

In some embodiments, combinations of binders may be used that may provide greater specificity or in certain embodiments amplification of the signal. Thus, in some embodiments, a sandwich of binders may be used, where the first binder may bind to the target and serve to provide for secondary binding, where the secondary binder may or may not include a signal generator, which may further provide for tertiary binding (if required) where the tertiary binding member may include a signal generator. Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse anti-xpress for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin. In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a signal generator before binding to the primary antibody or may be capable of binding to a signal generator at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a signal generator. The secondary antibody, avidin, streptavidin, or biotin may be each independently labeled with a signal generator.

Sequentially Analyzing a Biological Sample, Contacting and Binding the Probe

A biological sample may be contacted with a probe to physically bind the probe to a target in the biological sample. In some embodiments, a target may not be easily accessible for binding the probe and a biological sample may be further processed to facilitate the binding between the target and the binder (in the probe). In some embodiments, a probe may be contacted with the biological sample in the form of a solution. Depending on the nature of the binder, the target, and the binding between the two, sufficient contact time may be allowed. In some embodiments, an excess of binder molecules may be employed to ensure all the targets in the biological sample are bound. After a sufficient time has been providing for the binding action, the sample may be contacted with a wash solution (for example an appropriate buffer solution) to wash away any unbound probes. Depending on the concentration and type of probes used, a biological sample may be subjected to a number of washing steps with the same or different washing solutions being employed in each step.

In some embodiments, the biological sample may be contacted with more than one probe in the first contacting step. The plurality of probes may be capable of binding different targets in the biological sample. For example, a biological sample may include two targets: target1 and target2 and two sets of probes may be used in this instance: probe1 (having binder1 capable of binding to target1) and probe2 (having binder2 capable of binding to target2). A plurality of probes may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

The number of probes that may be simultaneously bound to the target may depend on the type of detection employed, that is, the spectral resolution achievable. For example, for fluorescence-based signal generators, at most four different probes (providing four spectrally resolvable fluorescent signals) may be employed in accordance with the methods disclosed herein. Spectrally resolvable, in reference to a plurality of fluorescent signal generators, implies that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems. In some embodiments, a biological sample may be essentially contacted with four or less than four probes in the first contacting step.

In some embodiments, a biological sample may include a whole cell, a tissue sample or a microarray. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuecan. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer. In some embodiments, a tissue section may be optionally subjected to a blocking step to minimize any non-specific binding.

Following the preparation of the tissue sample, a probe solution (e.g., labeled-antibody solution in an IHC procedure) may be contacted with the tissue section for a sufficient period of time and under conditions suitable for binding of binder to the target (e.g., antigen in an IHC procedure). As described earlier, two detection methods may be used: direct or indirect. In a direct detection, a signal generator-labeled primary antibody (e.g., fluorophore-labeled primary antibody) may be incubated with an antigen in the tissue sample, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In embodiments where the secondary antibody may be conjugated to an enzymatic label, a chromogenic or fluorogenic substrate may be added to provide visualization of the antigen. In some embodiments two or more (at most four) primary antibodies (labeled or unlabeled) may be contacted with the tissue sample. Unlabeled antibodies may be then contacted with the corresponding labeled secondary antibodies.

Technical effects of the disclosure include providing improved prognosis for patients based on immune cell type and localization. Such techniques may also be used to provide rapid automated immune scores. Further, the disclosed techniques may be used to generate an immune marker panel, a therapy assessment, and a biopsy assessment for a patient.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining distribution of immune cell populations in a biological sample comprising:
applying sequentially individual probes of a plurality of probes to a biological tissue sample obtained from a tumor region, each of the plurality of probes comprising a respective distinguishably detectable signal generator;
imaging each probe of the plurality of probes in a sequential manner to acquire image data of the biological sample representative of the plurality of probes bound to a respective plurality of target molecules in the biological sample based on distinguishable signals detected from each respective distinguishably detectable signal generator of the plurality of probes, wherein at least one of the plurality of probes comprises a first signal generator and is an epithelium probe, a membrane probe, a cytoplasm probe, or nuclear probe specific for a cell nucleus, wherein at least one of the plurality of probes comprises a second signal generator and is an immune probe specific for an immune marker, the plurality of target molecules comprises an epithelium target molecule, a membrane target molecule, a cytoplasm target molecule, or a nuclear target molecule and wherein the biological sample comprises the immune marker;
segmenting epithelial and stromal regions of the sample using the signals from the first signal generator to identify single cells within each region, wherein identifying single cells in the epithelial region or the stromal region comprises using image data of the first signal generator representative of the epithelium probe, the membrane probe, the cytoplasm probe, or the nuclear probe bound to at least one of the target molecules and wherein identification of single cells in the stromal region comprises segmenting the epithelial region of the sample to generate an epithelial mask and classifying regions not contained within the epithelial mask as one or more of the stromal region or background such that each cell of the single cells is assigned to either the epithelial region or the stromal region;
identifying immune cells among the single cells using signals from the second signal generator generating an immune probe signal representative of the immune probe bound to the immune marker, wherein identifying comprises reclassifying single cells in the sample as immune cells based on a signal intensity of the image data from the immune probe signal representative of the immune probe bound to the immune marker;
generating an immune marker positive epithelial fraction and an immune marker positive stromal fraction based on the identified immune cells among the single cells in the epithelial region and the stromal region;
determining a first standard deviation of the immune probe signal intensity for the immune marker in the epithelial region and a second standard deviation of the immune marker in the stromal region based on the image data of the immune probe bound to the immune marker in the epithelial region and the stromal region; and
determining a distribution, location, and type of a plurality of the immune cells in the biological sample based on the immune marker positive epithelial fraction relative to the immune marker positive stromal fraction and the first standard deviation or the second standard deviation.

2. The method of claim 1, wherein at least one of the plurality of probes comprises an epithelial probe specific for epithelial cells and wherein a signal generated by the epithelial probe is used to determine the epithelial region.

3. The method of claim 2, wherein the epithelial probe is used to create the epithelial mask.

4. The method of claim 3, wherein a region not defined by the epithelial mask is used to define a stromal mask.

5. The method of claim 4, wherein determining a distribution, location, and type of a plurality of immune cells in the biological sample comprises quantifying the immune cells within the stromal mask.

6. The method of claim 1, wherein determining a distribution, location, and type of a plurality of immune cells in the biological sample comprises quantifying the immune cells within the epithelial mask.

7. The method of claim 1, wherein intensity and morphology-based algorithms, generalized wavelet-based algorithms, or probabilistic-based methods are used to detect individual nuclei in the stromal region using the image data representative of the nuclear probe.

8. The method of claim 1, comprising removing a non-specific 4',6-diaminidino-2-phenylindole (DAPI) signal by using two-class clustering to identify positive DAPI nuclei in the stromal region.

9. The method of claim 1, wherein the plurality of probes comprise a plurality of immune probes specific for immune markers of immune cell subtypes and respective sub-type signal signerators, wherein the immune cells are characterized by an immune probe signal intensity of the sub-type signal generators above a threshold signal intensity, and wherein threshold values associated with a positive signal are determined for the immune markers of the immune cell subtypes.

10. The method of claim 1, wherein the immune cells are characterized by an immune probe signal intensity above a threshold signal intensity and wherein the threshold value is determined based on a box-plot or histogram or violin plot analysis of overall immune marker expression in stroma across all images for the sample set.

11. The method of claim 1, wherein the immune cells are characterized by an immune probe signal intensity above a threshold signal intensity and wherein the threshold is determined based on a predetermined quantile for overall expression of the immune marker and one or more of the target molecules in the epithelial or stromal region selected as the threshold value for a positive signal.

12. The method of claim 11, wherein the predetermined quantile is 80%-99%.

13. The method of claim 1, wherein determining a distribution, location, and type of a plurality of immune cells in the biological sample comprises determining a number of each cell of the single cells positive for the immune marker.

14. The method of claim 1, wherein the plurality of probes comprises a plurality of epithelial probes specific for epithelial markers and wherein segmenting the epithelial region of the tissue comprises using image data representative of the plurality of epithelial probes to produce a super-epithelium image.

15. The method of claim 14, wherein segmenting the epithelial region comprises smoothing the image data representative of the nuclear probe and applying an optimal global threshold for positive signal.

16. The method of claim 15, wherein small gaps in the super-epithelium image are filled using the image data representative of the nuclear probe.

17. The method of claim 1, wherein determining overall distribution, location, and type of immune cells comprises determining a number of cells of the single cells positive for the immune marker in the epithelial region.

18. The method of claim 1, comprising determining overall distribution patterns of immune cells in the epithelial region and the stromal region.

19. The method of claim 1, comprising determining overall distribution patterns of immune cells in a combined epithelial and stromal region.

20. The method of claim 1, comprising determining a ratio of immune cells in the epithelial region versus the stromal region.

21. The method of claim 1, comprising determining a patient survival associated with the biological sample based on the distribution, location, and type of immune cells.

22. The method of claim 1, comprising removing the immune cells from the data representative of the epithelial region and the stromal region.

* * * * *